(12) United States Patent
Krause et al.

(10) Patent No.: US 8,815,592 B2
(45) Date of Patent: Aug. 26, 2014

(54) METHODS AND COMPOSITIONS RELATED TO DOPAMINERGIC NEURONAL CELLS

(75) Inventors: Karl-Heinz Krause, Geneva (CH); Olivier Preynat-Seauve, Geneva (CH)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 13/696,775

(22) PCT Filed: Apr. 20, 2011

(86) PCT No.: PCT/US2011/033232
§ 371 (c)(1),
(2), (4) Date: Feb. 20, 2013

(87) PCT Pub. No.: WO2011/133661
PCT Pub. Date: Oct. 27, 2011

(65) Prior Publication Data
US 2013/0149717 A1    Jun. 13, 2013

Related U.S. Application Data

(60) Provisional application No. 61/326,403, filed on Apr. 21, 2010.

(51) Int. Cl.
| | | |
|---|---|---|
| *C12N 5/00* | (2006.01) | |
| *C12N 5/02* | (2006.01) | |
| *C07D 263/58* | (2006.01) | |
| *C07D 235/26* | (2006.01) | |
| *A61K 35/30* | (2006.01) | |
| *A61K 31/4184* | (2006.01) | |
| *A61K 31/423* | (2006.01) | |
| *C12N 5/0793* | (2010.01) | |

(52) U.S. Cl.
CPC ........ *C12N 5/0619* (2013.01); *C12N 2501/999* (2013.01); *C07D 263/58* (2013.01); *C07D 235/26* (2013.01); *C12N 2506/02* (2013.01); *A61K 35/30* (2013.01); *A61K 31/4184* (2013.01); *A61K 31/423* (2013.01)
USPC .......................................... 435/377; 435/325

(58) Field of Classification Search
USPC ................................................. 435/377, 325
See application file for complete search history.

(56) References Cited

U.S. PATENT DOCUMENTS

| | | | |
|---|---|---|---|
| 4,923,898 | A | 5/1990 | Sunshine et al. |
| 5,665,737 | A | 9/1997 | Cavalla et al. |
| 5,843,780 | A | 12/1998 | Thomson |
| 6,200,806 | B1 | 3/2001 | Thomson |
| 6,242,471 | B1 | 6/2001 | Yasuma et al. |
| 6,833,269 | B2 | 12/2004 | Carpenter |
| 7,029,913 | B2 | 4/2006 | Thomson |
| 7,250,294 | B2 | 7/2007 | Carpenter et al. |
| 2003/0211605 | A1 | 11/2003 | Lee et al. |
| 2004/0102435 | A1 | 5/2004 | Barlaam et al. |
| 2008/0045528 | A1 | 2/2008 | Sutton et al. |
| 2008/0233610 | A1 | 9/2008 | Thomson et al. |
| 2009/0012081 | A1 | 1/2009 | Okawa et al. |
| 2009/0076019 | A1* | 3/2009 | Tyers et al. ............... 514/252.13 |
| 2009/0082368 | A1 | 3/2009 | Vohra et al. |

FOREIGN PATENT DOCUMENTS

| | | | |
|---|---|---|---|
| EP | 1970446 | 9/2008 | |
| WO | WO 2004/105787 | * 12/2004 | ............. A61K 38/18 |
| WO | WO 2009/015667 | 2/2009 | |

OTHER PUBLICATIONS

Stem Cells: Scientific Progress and Future Directions. Department of Health and Human Services. Jun. 2001. Chapter 1: The Stem Cell. pp. 1-4.*
Search Result. Printout from search, 2013, pp. 1-10.*
Afonina et al., "Primers with 5' flaps improve real time PCR", *BioTechniques*, 43(6):770-773, 2007.
Barberi et al., "Neural subtype specification of fertilization and nuclear transfer embryonic stem cells and application in parkinsonian mice", *Nature Biotechnology*, 21(10):1200-1207, 2003.
Cao et al., "Modulation of recombinant small-conductance $Ca^{2+}$-activated $K^+$ channels by the muscle relaxant chlorzoxazone and structurally related compounds", *The Journal of Pharmacology and Experimental Therapeutics*, 296:683-689, 2001.
Huang et al., "The syneregistic inhibitory actions of oxcarbazepine on voltage-gated sodium and potassium currents in differentiated NG108-15 neuronal cells model neurons", *International Journal of Neuropsychopharmacology*, 11:597-610, 2008.
Itskovitz-Eldor et al., "Differentiation of human embryonic stem cells into embryroid bodies compromising the three embryonic germ layers", *Mol Med.*, 6(2):88-95.
Ji et al., "SK $Ca^{2+}$-activated $K^+$ channel ligands alter the firing pattern of dopamine-containing neurons in vivo" *Neuroscience*, 140:623-633, 2006.
Jia et al., "Transcription coactivator peroxisome proliferator-activated receptor-binding protein/mediator 1 deficiency abrogates acetaminophen hepatotoxicity", *Proc Natl Acad Sci USA*, 102(35):12531-6, 2005.
Jones et al., "Overexpression of a potassium channel gene perturbs neural differentiation", *J Neurosci.*, 14:2789-99, 1994.

(Continued)

*Primary Examiner* — Marcia S Noble

(74) *Attorney, Agent, or Firm* — Parker Highlander PLLC

(57) ABSTRACT

A method of differentiation stem cells cells by contacting stem cells with a dopaminergic differentiation agent is provided in certain aspects. For example, the agent may comprise substituted benzoxazole. These methods and compositions may be used in toxicological screens, e.g., to evaluate the neurotoxicity of a test compound or treatment of neurological disorders.

7 Claims, 19 Drawing Sheets

(56) References Cited

OTHER PUBLICATIONS

Koshimura et al., "Enhancement of neuronal survival by 6R-tetrahydrobiopterin", *Neuroscience*, 88(2):561-569, 1999.

Lukhtanov et al., "Novel DNA probes with low background and high hybridization-triggered fluorescence", *Nucleic Acids Research*, 35(5):e30, 2007.

Metallo et al., "Retinoic acid and bone morphogenetic protein signaling synergize to efficiently direct epithelial differentiation of human embryonic stem cells", *Stem Cells* 26(2):372-80, 2008.

PCT International Preliminary Report on Patentability issued in International Application No. PCT/US2011/033232, dated Oct. 23, 2012.

PCT International Search Report and Written Opinion issued in International Application No. PCT/US2011/033232, dated Dec. 19, 2011.

Reubinoff et al., "Embryonic stem cell lines from human blastocysts: somatic differentiation in vitro", *Nat Biotechnol.*, 18(4):399-404, 2000.

Smith, "Embryo-derived stem cells: of mice and men", *Annu Rev Cell Dev Biol.*, 14:435-62, 2001.

Syme et al., "Pharmacological activation of cloned intermediate- and small-conductance $Ca^{2+}$ activated $K^+$ channels", *Am J Physiol Cell Physiol.*, 278:C570-C581, 2000.

Takahashi et al., "Induction of pluripotent stem cells from adult human fibroblasts by defined factors", *Cells*, 131:861-72, 2007.

Takahashi et al., "Induction of pluripotent stem cells from mouse embryonic and adult fibroblast cultures by defined factors", *Cell*, 126:663-676, 2006.

Thomson et al., "Embryonic stem cell lines derived from human blastocysts", *Science* 282(5391):1145-7, 1998.

Thomson et al., "Isolation of a primate embryonic stem cell line", *Proc Natl Acad Sci USA*, 92(17):7844-8, 1995.

Xu et al., "Feeder-free growth of undifferentiated human embryonic stem cells", *Nat Biotechnol.*, 19(10):971-4, 2001.

Ying et al., "BMP induction of Id proteins suppresses differentiation and sustains embryonic stem cell self-renewal in collaboration with STAT3", *Cell*, 115(3):281-92.

Yu and Thomson, "Pluripotent stem cell lines", *Genes Dev.*, 22(15):1987-97, 2008.

Yu et al., "Induced pluripotent stem cell lines derived from human somatic cells", *Science*, 318:1917-20, 2007.

\* cited by examiner

METHODS AND COMPOSITIONS RELATED TO DOPAMINERGIC NEURONAL CELLS

This application is a national phase application under 35 U.S.C. §371 of International Application No. PCT/US2011/033232, filed Apr. 20, 2011, which claims priority to U.S. Application No. 61/326,403 filed on Apr. 21, 2010, the entire disclosure of which is specifically incorporated herein by reference in its entirety without disclaimer. This application is related to U.S. Application No. 61/007,334 filed on Dec. 11, 2007, the entire disclosure of which is specifically incorporated herein by reference in its entirety without disclaimer.

BACKGROUND OF THE INVENTION

1. Field of the Invention

This invention generally relates to the field of stem cell development, and in particular to the use of chemical agents to prepare populations of specific neurons, for example, dopaminergic neurons, and the applications of those neurons.

2. Related Art

Pluripotent stems cells, including embryonic stem (ES) cells and induced pluripotent stem cells, hold great promise for studying early development and for use in cell therapy. The same is true of adult and embryonic neural stem cells. Because such cells can proliferate in culture and maintain their potential for differentiating into different cell types, they can provide an almost unlimited supply of cells for treating a variety of diseases. A particularly active area of research is the treatment of nervous system diseases using cell therapy. One approach to the treatment of degenerative nervous system diseases is to transplant specific neurons, such as dopaminergic neurons, into affected areas of the nervous system.

Potential sources of those neural-lineage cells are cultures of specific neurons prepared by differentiating ES cells, induced pluripotent stem (iPS) cells and other types of stem cells in vitro. Methods of preparing primate ES cell cultures have been described for human, rhesus monkey, and marmoset ES cells (U.S. Pat. Nos. 5,843,780; 6,200,806; 7,029,913). The methods involve removing the trophoectoderm layers from blastocysts, then plating the remaining inner cell mass cells onto a feeder layer of gamma-irradiated mouse embryonic fibroblasts. After 7-21 days in culture, cell outgrowths are removed, dissociated, then replated onto embryonic feeder layers. Colonies that form are then picked, briefly trypsinized to dissociate, then replated on embryonic feeder layers. The cells can be routinely split every 1-2 weeks using brief trypsinization.

Unfortunately, although a heterogeneous mixture of different cell types derived from pluripotent stem cells is easy to obtain in culture, their targeted differentiation towards a specific lineage remains challenging. In general, spontaneous differentiation of ES cells in culture produces a heterogeneous mixture of cells, only some of which may be neural cells. Thus, spontaneous differentiation is not an effective means of providing specific neurons.

Small molecules have been tested for their ability to influence ES cell differentiation. For example, retinoic acid has been used to induce neuronal differentiation of ES cells. However, exposure to retinoic acid leads to differentiation mainly of glial cells, while human ES cells exposed to retinoic acid differentiate towards epithelial cells (Metallo et al., 2007). Generation of dopaminergic neurons from mouse embryonic stem cells (CGR8 line) is a promising tool for Parkinson's disease as a source for future cell therapy. Many protocols of dopaminergic differentiation of mouse embryonic stem cells (CGR8 line) are currently available. However, most procedures include generation of heterogeneous cell population that not sufficiently pure and efficient. Thus, additional compounds and alternative methods of neural differentiation from human ES cells and other types of stem cells are needed to exploit the uses of cell therapy for treatment of neurological diseases and neurotoxicity testing.

SUMMARY OF THE INVENTION

Most of the available methods of dopaminergic differentiation of mouse embryonic stem cells include a generation of heterogeneous cell population that not sufficiently pure and efficient. As shown in the below examples, zoxazolamine and its analogs were tested in mouse ES cells, which demonstrated their enhancing effect on dopaminergic differentiation. Aspects of the present invention provide compositions and methods for enhancing the efficiency of dopaminergic differentiation of stem cells, therefore allowing generation of efficient and reproducible population of dopaminergic neurons. Methods are also provided to develop a new platform for testing neurotoxcity of compounds that using the dopaminergic differentiation methods and compositions.

Therefore, in certain aspects, there is provided a method for preparing dopaminergic neuronal cells or differentiating stem cells in vitro comprising exposing one or more stem cells to a dopaminergic differentiation agent such as a substituted benzoxazole. Dopaminergic neural cells or cells expressing dopaminergic receptors could be prepared from the cells exposed to the dopaminergic differentiation agent. In certain aspects, the dopaminergic differentiation agent or the substituted benzoxazole may increase neurite outgrowth, neural differentiation or maturation, or dopaminergic specification of neurons. For example, the cells expressing dopaminergic markers (such as DAT) may increase in the presence of such an agent.

The dopaminegic differentiation agent may comprise a substituted benzoxazole of the formula:

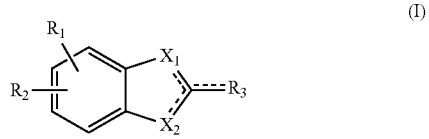

(I)

wherein:

$X_1$ and $X_2$ are independently: O, N, or N—$R_4$;

$R_1$ and $R_2$ are independently:

hydrogen, hydroxy, halo, amino, nitro, hydroxyamino, cyano, azido or mercapto; or alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heteroaralkyl$_{(C\leq 8)}$, fluoroalkyl$_{(C\leq 8)}$, acyl$_{(C\leq 8)}$, alkoxy$_{(C\leq 8)}$, alkenyloxy$_{(C\leq 8)}$, alkynyloxy$_{(C\leq 8)}$, aryloxy$_{(C\leq 8)}$, aralkoxy$_{(C\leq 8)}$, heteroaryloxy$_{(C\leq 8)}$, heteroaralkoxy$_{(C\leq 8)}$, acyloxy$_{(C\leq 8)}$, alkylamino$_{(C\leq 8)}$, dialkylamino$_{(C\leq 8)}$, alkoxyamino$_{(C\leq 8)}$, alkenylamino$_{(C\leq 8)}$, alkynylamino$_{(C\leq 8)}$, arylamino$_{(C\leq 8)}$, aralkylamino$_{(C\leq 8)}$, heteroarylamino$_{(C\leq 8)}$, heteroaralkylamino$_{(C\leq 8)}$, amido$_{(C\leq 8)}$, or a substituted version of any of these groups;

$R_3$ is:

hydroxy, oxo, halo, amino, nitro, hydroxyamino, cyano, azido or mercapto; or alkoxy$_{(C\leq 8)}$, alkenyloxy$_{(C\leq 8)}$, alkynyloxy$_{(C\leq 8)}$, aryloxy$_{(C\leq 8)}$, aralkoxy$_{(C\leq 8)}$, heteroaryloxy$_{(C\leq 8)}$, heteroaralkoxy$_{(C\leq 8)}$, acyloxy$_{(C\leq 8)}$, alkylamino$_{(C\leq 8)}$, dialkylamino$_{(C\leq8)}$, alkoxyamino$_{(C\leq8)}$, alkenylamino$_{(C\leq8)}$, alkynylamino$_{(C\leq8)}$, arylamino$_{(C\leq8)}$, aralkylamino$_{(C\leq8)}$, heteroarylamino$_{(C\leq8)}$, heteroaralkylamino$_{(C\leq8)}$, amido$_{(C\leq8)}$, or a substituted version of any of these groups; and R$_4$ is:
hydrogen, hydroxy, halo, amino, nitro, hydroxyamino, cyano, azido or mercapto; or
alkyl$_{(C\leq8)}$, alkenyl$_{(C\leq8)}$, alkynyl$_{(C\leq8)}$, aryl$_{(C\leq8)}$, aralkyl$_{(C\leq8)}$, arenediyl$_{(C\leq8)}$, heteroaryl$_{(C\leq8)}$, heteroaralkyl$_{(C\leq8)}$, acyl$_{(C\leq8)}$, alkoxy$_{(C\leq8)}$, alkenyloxy$_{(C\leq8)}$, alkynyloxy$_{(C\leq8)}$, aryloxy$_{(C\leq8)}$, aralkoxy$_{(C\leq8)}$, heteroaryloxy$_{(C\leq8)}$, heteroaralkoxy$_{(C\leq8)}$, acyloxy$_{(C\leq8)}$, alkylamino$_{(C\leq8)}$, dialkylamino$_{(C\leq8)}$, alkoxyamino$_{(C\leq8)}$, alkenylamino$_{(C\leq8)}$, alkynylamino$_{(C\leq8)}$, arylamino$_{(C\leq8)}$, aralkylamino$_{(C\leq8)}$, heteroarylamino$_{(C\leq8)}$, heteroaralkylamino$_{(C\leq8)}$, amido$_{(C\leq8)}$, or a substituted version of any of these groups;

or pharmaceutically acceptable salts or tautomers.

In certain aspects, the substituted benzoxazole has a formula of:

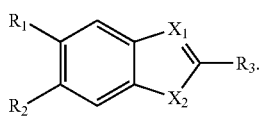

(II)

Specifically, R$_1$ and R$_2$ may be independently hydrogen or halo. For example, R$_1$ and R$_2$ may be hydrogen and chloro, respectively. In particular aspects, X$_1$ and X$_2$ may be independently N and O. In further aspects, R$_3$ may be hydroxy or amino.

In other aspects, the substituted benzoxazole has a formula of:

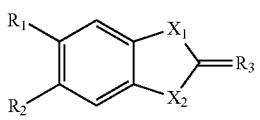

(III)

For example, R$_3$ is O. R$_1$ and R$_2$ may be independently H or trifluoromethyl. X$_1$ and X$_2$ may be independently N—R$_4$. For example, R$_4$ may be H, alkyl or arenediyl. Particularly, R$_4$ may be aryl such as (trifluoro)phenyl.

In one aspect, R$_1$ is chloro and R$_3$ is amino. In particular, the substituted benzoxazole is zoxazolamine or its structural analogs such as 5-chloro-2-hydroxybenzoxazole (chlorzoxazone), 1-ethyl-2-benzimidazolinone(1-EBIO), or 1,3-dihydro-1-[2-hydroxy-5-(trifluoromethyl)phenyl]-5-(trifluoromethyl)-2H-benzimidazol-2-one (NS 1619). In certain aspects, the substituted benzoxazole may not include 5-chloro-2-hydroxybenzoxazole (chlorzoxazone).

Zoxazolamine has the structure:

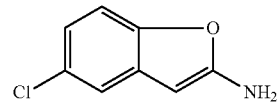

Chlorzoxazone has the structure:

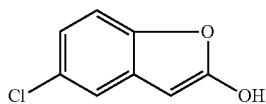 [SMILES: Oc1cc2cc(Cl)ccc2o1]

1-EBIO has the structure:

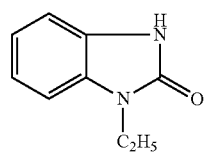

NS 1619 has the structure:

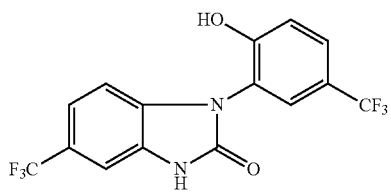 [SMILES: O=c1[nH]c2cc(C(F)(F)F)ccc2n1-c1cc(C(F)(F)F)ccc1O]

In certain aspects, the substituted benzoxazole may be a potassium channel modulator, such as a small-conductance Ca$^{2+}$-activated potassium channel modulator. In other aspects, the dopaminergic differentiation agent may comprise a potassium channel modulator, for example, a small-conductance Ca$^{2+}$-activated potassium channel modulator. Non-limiting examples of potassium channel modulators include zoxazolamine, chlorzoxazone, 1-EBIO, or NS 1619.

The inventors also contemplate any modulators of potassium channels, especially activators, could be used in certain aspects of the invention, e.g. to enhance dopaminergic differentiation. Indeed, zoxazolamine and its analogs all activate some families of potassium channels. Non-limiting examples of potassium channels activators include: NS309, CyPPA (Ca$^{2+}$ activated channels); all G-Protein Coupled Receptors agonists, diazoxide, pinacidil (inwardly rectifying channels); Halothane (tandem pore domain channels); Retigabine (voltage gated channels); or any potassium channels pharmacological modulator, such as described by the web link via world wide web at sigmaaldrich.com/catalog/ProductDetail.do?N4=LO22201SIGMA&N5=SEARCH_CONCAT_P NO|BRAND_KEY&F=SPEC.

In certain embodiments, the stem cells may be pluripotent stem cells, which can be embryonic stem (ES) cells, induced pluripotent stem cells, or embryonic stem cells derived by somatic cell nuclear transfer. In other embodiments, the stem cells are adult or embryonic neural stem cells. In preferred embodiments, the stem cells are obtained from a cell culture. The cell culture can be a primary cell culture, a subculture of a primary cell culture, or a cell line. Preferably, the stem cells are of mouse, primate, mammal, human or monkey origin. In some embodiments, the stem cells are ES cells obtained from an embryo or a blastocyst. In other embodiments, the stem cells are ES cells obtained from a cell culture of undifferentiated ES cells.

It is contemplated that the differentiation of virtually any pluripotent stem cell or cell line, e.g., human or mouse embryonic stem cells or induced pluripotent stem cells (iPS cells), may be promoted via contacting the cell with a dopaminergic differentiation agent (e.g., zoxazolamine). For example, human embryonic stem cell line H1, H9, hES2, hES3, hES4, hES5, hES6, BG01, BG02, BG03, HSF1, HSF6, H1, H7, H9, H13B, and/or H14 etc. may be used in various embodiments according to the present invention. It is further contemplated that stem cell lines which subsequently become available may also be utilized in certain embodiments of the present invention. In certain embodiments, the dopaminergic differentiation agent selectively promotes differentiation of the pluripotent cell into a dopaminergic neuronal cell.

In further embodiments, the stem cells are multipotent stem cells. For example, the stem cells can be neural stem cells or neural precursor cells. In a further aspect, the neural precursor cell is of mammalian origin, and is preferably a mouse, human or monkey cell. In certain embodiments, the neural precursor cell can be prepared by exposing pluripotent stem cells or neural stem cells to a neural differentiation agent as described below. In other embodiments, the neural precursor cell is obtained from a culture of neural precursor cells, such as a primary cell culture from brain tissue, or a culture of neural precursor cells differentiated in vitro. In certain embodiments, the stem cells may be exposed to a neural differentiation agent prior to, during or after the exposure to the dopaminergic differentiation agent. In some aspects, the stem cells or the progeny cells thereof may be exposed to a combination of the dopaminergic differentiation agent and the neural differentiation agent, for example, to optimize the generation of an engineered neural tissue (ENT).

For example, the neural differentiation agent is a compound having the structure (IV).

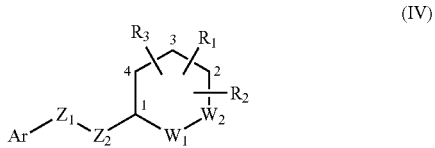

(IV)

In the compound of structure (IV), $Z_1$ and $Z_2$ are preferably both carbon triply bonded to each other, or preferably both nitrogen doubly bonded to each other. The neural differentiation agent can be: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl)diazenylpyridine-2,6-diamine; 3-[(2-methyl-1,3-thiazol-4-yl)ethynyl]pyridine (MTEP); a physiologically acceptable salt thereof; or any combination thereof.

In certain embodiments, any cells of the present invention may be exposed to the dopaminergic differentiation agent such as the substituted benzoxazole with a concentration of at least, at most or about 0.01, 0.1, 0.5, 1, 5, 10, 15, 20, 25, 30, 35, 40, 45, 50, 55, 60, 65, 70, 75, 80, 85, 90, 95, 100 μM or any range derivable therein, or any effective amount. In a further embodiment, any cells of the present invention may be exposed to the dopaminergic differentiation agent such as the substituted benzoxazole for a period of time of at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 days or any range derivable therein. Any cells of the present invention may be exposed to the dopaminergic differentiation agent while in a suspension culture or in an adherent culture.

In further embodiments, any cells of the present invention may be exposed to the neural differentiation agent such as the compound of structure (IV) with a concentration of at least, at most or about 0.01, 0.1, 0.5, 1, 5, 10, 15, 20, 25, 30, 35, 40, 45, 50, 55, 60, 65, 70, 75, 80, 85, 90, 95, 100 μM or any range derivable therein, or any effective amount. In a still further embodiment, any cells of the present invention may be exposed to the neural differentiation agent for a period of time of at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 days or any range derivable therein. Any cells of the present invention may be exposed to the neural differentiation agent while in a suspension culture or in an adherent culture.

Aspects of the present invention may also include methods comprising evaluating the cells such as progeny of the stem cells for one or more characteristics of dopaminergic neuronal cells. Evaluation of the characteristics may identify one or more of the cells as dopaminergic neuronal cells. The characteristics may include an ability to bind dopamine transporter (DAT), electrophysiological characteristics, or expression of one or more dopaminergic markers, such as tyrosine hydroxylase (TH), dopaminergic transporter (DAT), G protein-activated inward rectifier potassium channel 2 (GIRK2), nuclear receptor related 1 (Nurr-1), Pitx3, the capacity of cells to uptake radioactive dopamine (specific for dopaminergic neurons), and also the measurement of secreted dopamine (e.g., by chromatography or electrodes).

In certain embodiments, the method may further comprise enriching or screening for dopaminergic neural cells. The enriching or screening may be performed during or subsequent to exposing the stem cells to a dopaminergic differentiation agent of the invention. Enriching for dopaminergic neural cells may comprise flow cytometry, magnetic cell sorting, or mechanic purification. Screening for dopaminergic neural cells may comprise screening for cells expressing one or more dopaminergic markers. In a further embodiment, the stem cells may be also exposed to a Rho-associated kinase (ROCK) inhibitor prior to, during, or after exposure to a dopaminergic differentiation agent.

The methods described above may further comprise assaying for a pharmacological or toxicological property of a test compound on the dopaminergic neuronal cells during or subsequent to contacting the dopaminergic neuronal cells with the test compound. In a further aspect, there is also provided a method of measuring a pharmacological or toxicological property (e.g., neurotoxicity) of a test compound. The method may comprise contacting the dopaminergic neural cells with the test compound. The dopaminergic neural cells may be comprised in an engineered neural tissue (ENT). Electrophysiology property, calcium signaling, cell survival, oxidative stress, or neural function of the dopaminergic neural cells may be measured during or subsequent to the contacting.

Any of the methods described herein may be automated or high-throughput or may comprise an automated or a high-throughput method. For example, the assay for a pharmacological or toxicological property of a test compound on the dopaminergic neuronal cells may be automated. In a further aspect, the dopaminergic neural cells may be assayed on an electrode array to monitor electrophysiological property. For example, the electrode array may be a multi- or micro-electrode array (MEA). Such an assay may be performed in the presence or absence of a test compound or prior to, during or after treatment of a test compound.

The dopaminergic neural cells or stem cells or any cells of the present invention may transgenically express a protein marker or tag, such as a luminescent or fluorescent protein. The luminescent or fluorescent protein may be selected from the group consisting of GFP, eGFP, EBFP, EBFP2, Azurite, mKalama1, ECFP, Cerulean, CyPet, YFP, Citrine, Venus, YPet, firefly luciferase (Fluc) and *Renilla* luciferase (Rluc). Expression of the luminescent or fluorescent protein may be measured optically or via fluorescence activated cell sorting (FACS).

Differentiation of one or more stem cells may also be promoted by contacting the stem cells with an effective amount of a dopaminergic differentiation agent of the present invention as describe above.

In a specific aspect, the stem cells to be differentiated may be induced pluripotent cells. Induced pluripotent stem cells, commonly abbreviated as iPS cells or iPSCs, are a type of pluripotent stem cell artificially derived from a non-pluripotent cell, typically an adult somatic cell, by inserting certain genes, such as a combination of Oct4, Sox2, Nanog, and Lin28, or a combination of Oct 3/4, Sox2, Klf4, and c-myc. Induced pluripotent stem cells are believed to be essentially identical to natural pluripotent stem cells, such as embryonic stem cells, in many respects including the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed. IPS cells have been described previously (see, e.g., Takahashi et al., 2006; Takahashi et al., 2007; Yu et al, 2007). Generation of iPS cells is described, e.g., in U.S. Patent Application 2008/0233610 and European Patent Application EP1970446A1, which are incorporated herein by reference in their entirety.

A cell population comprising dopaminergic neural cells prepared by exposure of stem cells to the dopaminergic differentiation agent can have various characteristics. In certain embodiments, the dopaminergic neural cells are synchronized such that a population of synchronized dopaminergic neural cells is provided. In other embodiments, non-dopaminergic neural cells and undifferentiated cells are eliminated from cultures such that a more homogeneous population of dopaminergic neural cells is provided.

In another aspect, the present invention provides a cell population comprising dopaminergic neural cells prepared by the forgoing method of preparing one or more neural precursor cells in vitro. There may also be provided a cell population comprising between about 10% and about 40% dopaminergic neural cells. Any of the cell population of the present invention may comprise at least, about or at most 10, 15, 20, 25, 30, 35, 40, 45, 50, 55, 60, 65, 70, 75, 80, 85, 90, 95, 99% dopaminergic neural cells or any range derivable therein.

In a further aspect, there is also provided a composition comprising a cell population comprising dopaminergic neural cells and a detectable amount of a substituted benzoxazole having the formula (I), (II) or (III), or pharmaceutically acceptable salts, tautomers, or optical isomers thereof as described above. For example, the detectable amount of the substituted benzoxazole may be at least, about, or up to 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95 µM or any range derivable therein. In particular, the substituted benzoxazole may be present at a concentration of about 1 to 20 µM.

For a cell replacement or regeneration therapy, certain aspects of the invention also provide a method for treating a subject having or at risk of a neural order such as a dopaminergic neuron disorder comprising administering to the subject with a population of dopaminergic neural cells prepared by the forgoing method or with a dopaminergic differentiation agent described above. The dopaminergic neuron disorder may be any neurological disorder having injured dopaminergic neurons, or a loss of function or number of dopaminergic neurons. The dopaminergic neuron disorder may be any disease associated with neural loss, such as Parkinson's disease. The subject may be a human, mouse, or primate. The method may further comprise diagnosing or identifying a subject with a dopaminergic neuron disorder.

The novel features which are believed to be characteristic of the invention, both as to its organization and method of operation, together with further objects and advantages will be better understood from the following description when considered in connection with the accompanying figures. It is to be expressly understood, however, that each of the figures and examples is provided for the purpose of illustration and description only and is not intended as a definition of the limits of the present invention It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

I. Definitions

Figure 1:
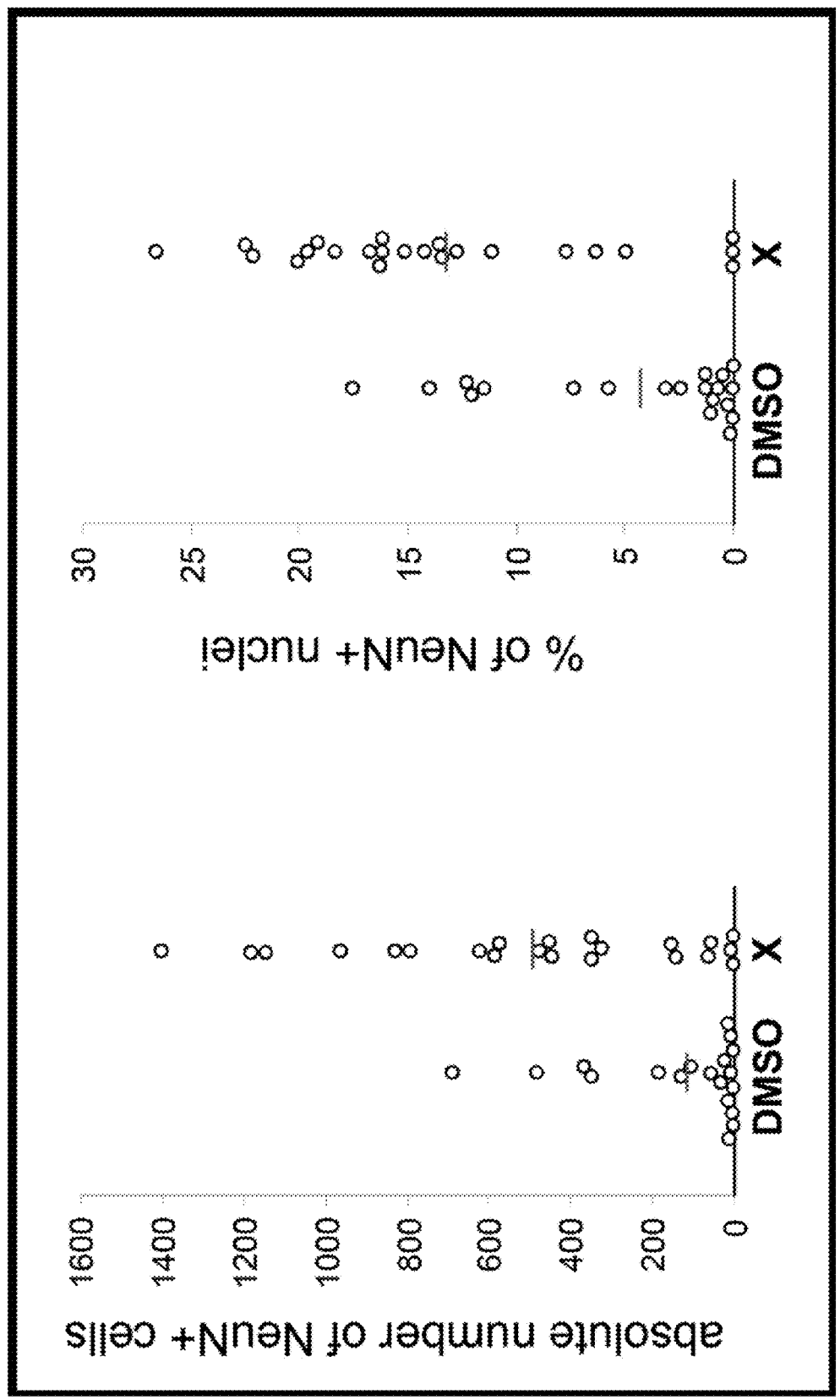
FIG. 1. Zoxazolamine increased neural differentiation of mouse embryonic stem cells (ESC). CGR8 line was differentiated on a monolayer of irradiated stromal PA6 at 1000 cells/well in 6 well plate culture in the presence of DMSO (vehicle) or 10 µM zoxazolamine. Cells were immunostained for neuronal markers after 2 weeks.

As used herein, the term "dopaminergic differentiation agent" means one or more compounds that enhance the differentiation of stem cells to dopaminergic neurons or the number of cells expressing dopaminergic neuron markers without any restriction as to the mode of action of the compound(s). Similarly, the term "neural differentiation agent" means one or more compounds that enhance the differentiation of stem cells to neural lineage cells without any restriction as to the mode of action of the compound(s). For example, without being bound by any theory, the dopaminergic differentiation agent or neural differentiation agent may assist the differentiation process by acting on a cell surface receptor, acting in the nucleus to regulate gene expression, acting on a protein in the cytoplasm, inducing or assisting a change in cell phenotype, promoting growth of cells with a particular phenotype or retarding the growth of others, or acting in concert with other agents through unknown mechanisms.

The term "a stem cell," including a precursor cell, refers to a cell that can generate at least two given cell types of fully differentiated functional cell. The role of stem cells in vivo is to replace cells that are destroyed during the normal life of an animal. Generally, stem cells can divide without limit. After division, the stem cell may remain as a stem cell or proceed to terminal differentiation. Although appearing morphologically unspecialized, the stem cell may be considered differentiated where the possibilities for further differentiation are limited.

"Embryonic stem (ES) cells" refers to cells isolated from the inner cell mass of the developing blastocyst. "ES cells" can be derived from any organism. ES cells can be derived from any mammals, including mice, rats, rabbits, guinea pigs, goats, pigs, cows and humans. Human and murine derived ES cells are preferred. ES cells are pluripotent cells, meaning that they can generate all of the cells present in any of the three germ layers (bone, muscle, brain cells, etc.).

As used herein, the term "differentiation" refers to the process whereby relatively unspecialized cells (e.g., embryonic cells) acquire specialized structural and/or functional features characteristic of mature cells. Typically, during differentiation, cellular structure alters and tissue-specific proteins appear.

An "effective amount" of agent is an amount sufficient to perform its intended function, for example, to differentiate stem cells or to prevent, treat, reduce and/or ameliorate the symptoms and/or underlying causes of any disorders or diseases. In some instances, an "effective amount" is sufficient to eliminate the symptoms of those diseases and, perhaps, overcome the disease itself.

"Treat", "Treating", "Treatment" and "Therapy" refer to any one or more of reducing or eliminating the symptoms of a particular disorder, slowing the progression, attenuating or curing an existing disease.

The term "subject" or "patient" as used herein generally refers to any warm blooded mammal, such as humans, non-human primates, rodents and the like which is to be the recipient of the particular treatment.

II. Differentiation Agents and Chemical Groups

In certain embodiments of the present invention, stem cells such as pluripotent stem cells, neural stem cells or neural precursor cells are exposed to a dopaminergic differentiation agent for the preparation of dopaminergic neurons.

In certain aspects, a dopaminergic differentiation agent in accordance with the present invention comprises a substituted benzoxazole having the following structure (I):

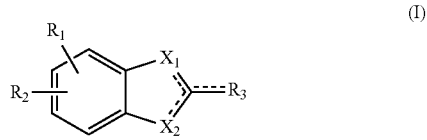

wherein:

$X_1$ and $X_2$ are independently: O, N, or N—$R_4$;

$R_1$ and $R_2$ are independently:
hydrogen, hydroxy, halo, amino, nitro, hydroxyamino, cyano, azido or mercapto; or
alkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heteroaralkyl$_{(C \leq 8)}$, fluoroalkyl$_{(C \leq 8)}$, acyl$_{(C \leq 8)}$, alkoxy$_{(C \leq 8)}$, alkenyloxy$_{(C \leq 8)}$, alkynyloxy$_{(C \leq 8)}$, aryloxy$_{(C \leq 8)}$, aralkoxy$_{(C \leq 8)}$, heteroaryloxy$_{(C \leq 8)}$, heteroaralkoxy$_{(C \leq 8)}$, acyloxy$_{(C \leq 8)}$, alkylamino$_{(C \leq 8)}$, dialkylamino$_{(C \leq 8)}$, alkoxyamino$_{(C \leq 8)}$, alkenylamino$_{(C \leq 8)}$, alkynylamino$_{(C \leq 8)}$, arylamino$_{(C \leq 8)}$, aralkylamino$_{(C \leq 8)}$, heteroarylamino$_{(C \leq 8)}$, heteroaralkylamino$_{(C \leq 8)}$, amido$_{(C \leq 8)}$, or a substituted version of any of these groups;

$R_3$ is:
hydroxy, oxo, halo, amino, nitro, hydroxyamino, cyano, azido or mercapto; or
alkoxy$_{(C \leq 8)}$, alkenyloxy$_{(C \leq 8)}$, alkynyloxy$_{(C \leq 8)}$, aryloxy$_{(C \leq 8)}$, aralkoxy$_{(C \leq 8)}$, heteroaryloxy$_{(C \leq 8)}$, heteroaralkoxy$_{(C \leq 8)}$, acyloxy$_{(C \leq 8)}$, alkylamino$_{(C \leq 8)}$, dialkylamino$_{(C \leq 8)}$, alkoxyamino$_{(C \leq 8)}$, alkenylamino$_{(C \leq 8)}$, alkynylamino$_{(C \leq 8)}$, arylamino$_{(C \leq 8)}$, aralkylamino$_{(C \leq 8)}$, heteroarylamino$_{(C \leq 8)}$, heteroaralkylamino$_{(C \leq 8)}$, amido$_{(C \leq 8)}$, or a substituted version of any of these groups; and $R_4$ is:
hydrogen, hydroxy, halo, amino, nitro, hydroxyamino, cyano, azido or mercapto; or
alkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, arenediyl$_{(C \leq 8)}$, heteroaryl$_{(C \leq 8)}$, heteroaralkyl$_{(C \leq 8)}$, acyl$_{(C \leq 8)}$, alkoxy$_{(C \leq 8)}$, alkenyloxy$_{(C \leq 8)}$, alkynyloxy$_{(C \leq 8)}$, aryloxy$_{(C \leq 8)}$, aralkoxy$_{(C \leq 8)}$, heteroaryloxy$_{(C \leq 8)}$, heteroaralkoxy$_{(C \leq 8)}$, acyloxy$_{(C \leq 8)}$, alkylamino$_{(C \leq 8)}$, dialkylamino$_{(C \leq 8)}$, alkoxyamino$_{(C \leq 8)}$, alkenylamino$_{(C \leq 8)}$, alkynylamino$_{(C \leq 8)}$, arylamino$_{(C \leq 8)}$, aralkylamino$_{(C \leq 8)}$, heteroarylamino$_{(C \leq 8)}$, heteroaralkylamino$_{(C \leq 8)}$, amido$_{(C \leq 8)}$, or a substituted version of any of these groups;

or pharmaceutically acceptable salts or tautomers.

In certain embodiments of structure (I), $R_1$ is chloro and $R_3$ is amino. Examples of structure (I) include zoxazolamine or its analogs such as chlorzoxazone, 1-EBIO, or NS1619.

In some embodiments of the present invention, stem cells may be also exposed to a neural differentiation agent for the preparation of engineered neural tissues prior to, during, after the exposure to the dopaminergic differentiation agent. In further embodiments, substantially undifferentiated stem cells or undifferentiated stem cells such as pluripotent stem cells may be exposed to a neural differentiation agent for the preparation of neural precursor cells, which may be followed by differentiation into dopaminergic neurons in the presence of a dopaminergic differentiation agent as described above.

In certain aspects, a neural differentiation agent in accordance with the present invention is a compound having the following structure (IV):

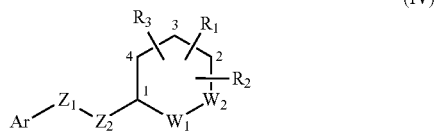

wherein:
the six membered ring defined by $W_1$, $W_2$ and carbon atoms 1, 2, 3 and 4, may be aromatic or non-aromatic, and further wherein any two neighboring atoms of this six membered ring may be singly or doubly bonded to one another;
$Z_1$ and $Z_2$ are either carbon or nitrogen, further wherein $Z_1$ and $Z_2$ may be singly, doubly, or triply bonded to one another and wherein $Z_2$ and carbon atom 1 may be singly or doubly bonded to one another, provided that the bond between $Z_1$ and $Z_2$ is not triple when $Z_1$ and $Z_2$ are nitrogen, further provided that the bond between $Z_1$ and $Z_2$ is single when the bond between $Z_2$ and carbon atom 1 is double;
Ar is a heteroatom-substituted or heteroatom-unsubstituted aryl$_{(C1-C12)}$;
one of either $W_1$ and $W_2$ is nitrogen and the other is carbon;
$R_1$, $R_2$, and $R_3$ are independently hydrogen, hydroxy, amino, cyano, halo, nitro, mercapto, or a heteroatom-substituted or heteroatom-unsubstituted alkyl$_{(C1-C8)}$, aryl$_{(C1-C8)}$, aralkyl$_{(C2-C8)}$, acyl$_{(C1-C8)}$, alkoxy$_{(C1-C8)}$, alkylamino$_{(C1-C8)}$, or =O;
or pharmaceutically acceptable salts, hydrates, tautomers, acetals, ketals, hemiacetals, hemiketals, or optical isomers thereof.

In preferred embodiments of structure (IV), $Z_1$ and $Z_2$ are both carbon triply bonded to each other. In other preferred embodiments of structure (IV), $Z_1$ and $Z_2$ are both nitrogen doubly bonded to each other.

Particularly preferred embodiments of structure (IV) include: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl)diazenylpyridine-2,6-diamine; 3-[(2-methyl-1,3-thiazol-4-yl)ethynyl]pyridine (MTEP); a physiologically acceptable salt thereof; or any combination thereof.

As used in any of structure (I)-(IV), the term "hydrogen" means H; the term "amino" means —NH$_2$; the term "nitro" means —NO$_2$; the term "oxo" means =O; the term "halo" designates —F, —Cl, —Br or —I; the term "mercapto" means —SH; the term "hydroxyamino" means —NHOH; the term "cyano" means —CN; the term "azido" means —N$_3$; the term "silyl" means —SiH$_3$, and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted alkyl$_{(Cn)}$, and heteroatom-substituted alkyl$_{(Cn)}$. The term "heteroatom-unsubstituted alkyl$_{(Cn)}$" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted alkyl$_{(C1-C10)}$ has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, and cyclohexyl, are all non-limiting examples of heteroatom-unsubstituted alkyl groups. The term "heteroatom-substituted alkyl$_{(Cn)}$" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted alkyl$_{(C1-C10)}$ has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" includes straight-chain alkanediyl, branched-chain alkanediyl, cycloalkanediyl, cyclic alkanediyl, heteroatom-unsubstituted alkanediyl, heteroatom-substituted alkanediyl, heteroatom-unsubstituted alkanediyl$_{(Cn)}$, and heteroatom-substituted alkanediyl$_{(Cn)}$. The term "heteroatom-unsubstituted alkanediyl$_{(Cn)}$" refers to a diradical, having a linear or branched, cyclic or acyclic structure, further having no carbon-carbon double or triple bonds, further having a total of n carbon atoms, all of which are nonaromatic, 2 or more hydrogen atoms, and no heteroatoms. For example, a heteroatom-unsubstituted alkanediyl$_{(C1-C10)}$ has 1 to 10 carbon atoms. The groups, —CH$_2$— (methylene), —CH$_2$CH$_2$—, and —CH$_2$CH$_2$CH$_2$—, are all non-limiting examples of heteroatom-unsubstituted alkanediyl groups. The term "heteroatom-substituted alkanediyl$_{(Cn)}$" refers to a radical, having two points of attachment to one or two saturated carbon atoms, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted alkanediyl$_{(C1-C10)}$ has 1 to 10 carbon atoms. The following groups are all non-limiting examples of heteroatom-substituted alkanediyl groups: —CH(F)—, —CF$_2$—, —CH(Cl)—, —CH(OH)—, —CH(OCH$_3$)—, and —CH$_2$CH(Cl)—.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted alkenyl$_{(Cn)}$, and heteroatom-substituted alkenyl$_{(Cn)}$. The term "heteroatom-unsubstituted alkenyl$_{(Cn)}$" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted alkenyl$_{(C2-C10)}$ has 2 to 10 carbon atoms. Heteroatom-unsubstituted alkenyl groups include: —CH=CH$_2$ (vinyl), —CH=CHCH$_3$, —CH=CHCH$_2$CH$_3$, —CH₂CH=CH₂ (allyl), —CH₂CH=CHCH₃, and —CH=CH—C₆H₅. The term "heteroatom-substituted alkenyl$_{(Cn)}$" refers to a radical, having a single nonaromatic carbon atom as the point of attachment and at least one non-aromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted alkenyl$_{(C2-C10)}$ has 2 to 10 carbon atoms. The groups, —CH=CHF, —CH=CHCl and —CH=CHBr, are non-limiting examples of heteroatom-substituted alkenyl groups.

The term "alkynyl" includes straight-chain alkynyl, branched-chain alkynyl, cycloalkynyl, cyclic alkynyl, heteroatom-unsubstituted alkynyl, heteroatom-substituted alkynyl, heteroatom-unsubstituted alkynyl$_{(Cn)}$, and heteroatom-substituted alkynyl$_{(Cn)}$. The term "heteroatom-unsubstituted alkynyl$_{(Cn)}$" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted alkynyl$_{(C2-C10)}$ has 2 to 10 carbon atoms. The groups, —C≡CH, —C≡CCH₃, and —C≡CC₆H₅ are non-limiting examples of heteroatom-unsubstituted alkynyl groups. The term "heteroatom-substituted alkynyl$_{(Cn)}$" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted alkynyl$_{(C2-C10)}$ has 2 to 10 carbon atoms. The group, —C≡CSi(CH₃)₃, is a non-limiting example of a heteroatom-substituted alkynyl group.

The term "aryl" includes heteroatom-unsubstituted aryl, heteroatom-substituted aryl, heteroatom-unsubstituted Cn-aryl, heteroatom-substituted Cn-aryl, heteroaryl, heterocyclic aryl groups, carbocyclic aryl groups, biaryl groups, and single-valent radicals derived from polycyclic fused hydrocarbons (PAHs). Non-limiting examples of heteroatom-unsubstituted aryl groups include phenyl (Ph), methylphenyl, (dimethyl)phenyl, —C₆H₄CH₂CH₃, —C₆H₄CH₂CH₂CH₃, —C₆H₄CH(CH₃)₂, —C₆H₄CH(CH₂)₂, —C₆H₃(CH₃) CH₂CH₃, —C₆H₄CH=CH₂, —C₆H₄CH=CHCH₃, —C₆H₄C≡CH, —C₆H₄C≡CCH₃, naphthyl, and the radical derived from biphenyl. The term "heteroatom-substituted Cn-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-substituted heteroaryl $_{(C1-C10)}$ has 1 to 10 carbon atoms. Non-limiting examples of heteroatom-substituted aryl groups include the groups: —C₆H₄F, —C₆H₄Cl, —C₆H₄Br, —C₆H₄I, —C₆H₄OH, —C₆H₄OCH₃, —C₆H₄OCH₂CH₃, —C₆H₄OC(O)CH₃, —C₆H₄NH₂, —C₆H₄NHCH₃, —C₆H₄N(CH₃)₂, —C₆H₄CH₂OH, —C₆H₄CH₂OC(O)CH₃, —C₆H₄CH₂NH₂, —C₆H₄CF₃, —C₆H₄CN, —C₆H₄CHO, —C₆H₄CHO, —C₆H₄C(O)CH₃, —C₆H₄C(O)C₆H₅, —C₆H₄CO₂H, —C₆H₄CO₂CH₃, —C₆H₄CONH₂, —C₆H₄CONHCH₃, —C₆H₄CON(CH₃)₂, furanyl, thienyl, pyridyl, pyrrolyl, pyrimidyl, pyrazinyl, quinolyl, indolyl, and imidazoyl. A particular example of substituted arenediyl may be (trifluomethyl)phenyl.

The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

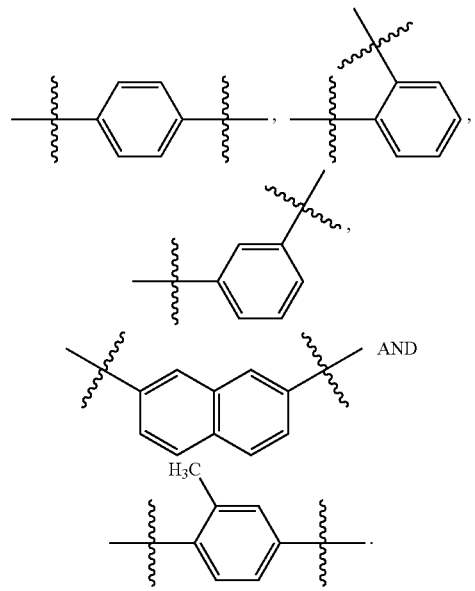

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —N(CH₃)₂, —C(O)NH₂, —OC(O)CH₃, or trifluomethyl. An "arene" refers to the compound H—R, wherein R is aryl.

The term "fluoroalkyl" when used without the "substituted" modifier refers to an alkyl, as that term is defined above, in which one or more fluorines have been substituted for hydrogens. The groups, —CH₂F, —CF₂H, —CF₃, and —CH₂CF₃ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "aralkyl" includes heteroatom-unsubstituted aralkyl$_{(Cn)}$, heteroatom-substituted aralkyl$_{(Cn)}$, heteroaralkyl, and heterocyclic aralkyl groups. The term "heteroatom-unsubstituted aralkyl$_{(Cn)}$" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted aralkyl$_{(C7-C10)}$ has 7 to 10 carbon atoms. Non-limiting examples of heteroatom-unsubstituted aralkyls are: phenylmethyl (benzyl, Bn) and phenylethyl. The term "heteroatom-substituted aralkyl$_{(Cn)}$" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted heteroaralkyl$_{(C2-C10)}$ has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted acyl$_{(Cn)}$, heteroatom-substituted acyl$_{(Cn)}$, alkylcarbonyl, alkoxycarbonyl and aminocarbonyl groups. The term "heteroatom-unsubstituted acyl$_{(Cn)}$" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted acyl$_{(C1-C10)}$ has 1 to 10 carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted acyl$_{(Cn)}$" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted acyl$_{(C1-C10)}$ has 1 to 10 carbon atoms. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted alkoxy$_{(Cn)}$, and heteroatom-substituted alkoxy$_{(Cn)}$. The term "heteroatom-unsubstituted alkoxy$_{(Cn)}$" refers to a group, having the structure —OR, in which R is a heteroatom-unsubstituted alkyl$_{(Cn)}$, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted alkoxy$_{(Cn)}$" refers to a group, having the structure —OR, in which R is a heteroatom-substituted alkyl$_{(Cn)}$, as that term is defined above. For example, —OCH$_2$CF$_3$ is a heteroatom-substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted alkenyloxy$_{(Cn)}$, and heteroatom-substituted alkenyloxy$_{(Cn)}$. The term "heteroatom-unsubstituted alkenyloxy$_{(Cn)}$" refers to a group, having the structure —OR, in which R is a heteroatom-unsubstituted alkenyl$_{(Cn)}$, as that term is defined above. The term "heteroatom-substituted alkenyloxy$_{(Cn)}$" refers to a group, having the structure —OR, in which R is a heteroatom-substituted alkenyl$_{(Cn)}$, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted alkynyloxy$_{(Cn)}$, and heteroatom-substituted alkynyloxy$_{(Cn)}$. The term "heteroatom-unsubstituted alkynyloxy$_{(Cn)}$" refers to a group, having the structure —OR, in which R is a heteroatom-unsubstituted alkynyl$_{(Cn)}$, as that term is defined above. The term "heteroatom-substituted alkynyloxy$_{(Cn)}$" refers to a group, having the structure —OR, in which R is a heteroatom-substituted alkynyl$_{(Cn)}$, as that term is defined above.

The term "aryloxy" includes heteroatom-unsubstituted aryloxy, heteroatom-substituted aryloxy, heteroatom-unsubstituted aryloxy$_{(Cn)}$, heteroatom-substituted aryloxy$_{(Cn)}$, heteroaryloxy, and heterocyclic aryloxy groups. The term "heteroatom-unsubstituted aryloxy$_{(Cn)}$" refers to a group, having the structure —OAr, in which Ar is a heteroatom-unsubstituted aryl$_{(Cn)}$, as that term is defined above. A non-limiting example of a heteroatom-unsubstituted aryloxy group is —OC$_6$H$_5$. The term "heteroatom-substituted aryloxy$_{(Cn)}$" refers to a group, having the structure —OAr, in which Ar is a heteroatom-substituted aryl$_{(Cn)}$, as that term is defined above.

The term "aralkyloxy" includes heteroatom-unsubstituted aralkyloxy, heteroatom-substituted aralkyloxy, heteroatom-unsubstituted aralkyloxy$_{(Cn)}$, heteroatom-substituted aralkyloxy$_{(Cn)}$, heteroaralkyloxy, and heterocyclic aralkyloxy groups. The term "heteroatom-unsubstituted aralkyloxy$_{(Cn)}$" refers to a group, having the structure —OAr, in which Ar is a heteroatom-unsubstituted aralkyl$_{(Cn)}$, as that term is defined above. The term "heteroatom-substituted aralkyloxy$_{(Cn)}$" refers to a group, having the structure OAr, in which Ar is a heteroatom-substituted aralkyl$_{(Cn)}$, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted acyloxy$_{(Cn)}$, heteroatom-substituted acyloxy$_{(Cn)}$, alkylcarbonyloxy, arylcarbonyloxy, alkoxycarbonyloxy, aryloxycarbonyloxy, and carboxylate groups. The term "heteroatom-unsubstituted acyloxy$_{(Cn)}$" refers to a group, having the structure —OAc, in which Ac is a heteroatom-unsubstituted acyl$_{(Cn)}$, as that term is defined above. For example, —OC(O)CH$_3$ is a non-limiting example of a heteroatom-unsubstituted acyloxy group. The term "heteroatom-substituted acyloxy$_{(Cn)}$" refers to a group, having the structure —OAc, in which Ac is a heteroatom-substituted acyl$_{(Cn)}$, as that term is defined above. For example, —OC(O)OCH$_3$ and —OC(O)NHCH$_3$ are non-limiting examples of heteroatom-unsubstituted acyloxy groups.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC($CH_3$)$_3$, —N($CH_3$)$CH_2CH_3$, —N($CH_2CH_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NH$C_6H_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted alkylamino$_{(Cn)}$, and heteroatom-substituted alkylamino$_{(Cn)}$. The term "heteroatom-unsubstituted alkylamino$_{(Cn)}$" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted alkylamino$_{(C1-C10)}$ has 1 to 10 carbon atoms. The term "heteroatom-unsubstituted alkylamino$_{(Cn)}$" includes groups, having the structure —NHR, in which R is a heteroatom-unsubstituted alkyl$_{(Cn)}$, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted alkylamino$_{(Cn)}$" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkylamino$_{(C1-C10)}$ has 1 to 10 carbon atoms. The term "heteroatom-substituted alkylamino$_{(Cn)}$" includes groups, having the structure 13 NHR, in which R is a heteroatom-substituted alkyl$_{(Cn)}$, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted alkenylamino$_{(Cn)}$, heteroatom-substituted alkenylamino$_{(Cn)}$, dialkenylamino, and alkyl(alkenyl)amino groups. The term "heteroatom-unsubstituted alkenylamino$_{(Cn)}$" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted alkenylamino$_{(C2-C10)}$ has 2 to 10 carbon atoms. The term "heteroatom-unsubstituted alkenylamino$_{(Cn)}$" includes groups, having the structure —NHR, in which R is a heteroatom-unsubstituted alkenyl$_{(Cn)}$, as that term is defined above. The term "heteroatom-substituted alkenylamino$_{(Cn)}$" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkenylamino$_{(C2-C10)}$ has 2 to 10 carbon atoms. The term "heteroatom-substituted alkenylamino$_{(Cn)}$" includes groups, having the structure —NHR, in which R is a heteroatom-substituted alkenyl$_{(Cn)}$, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted alkynylamino$_{(Cn)}$, heteroatom-substituted alkynylamino$_{(Cn)}$, dialkynylamino, alkyl(alkynyl)amino, and alkenyl(alkynyl)amino groups. The term "heteroatom-unsubstituted alkynylamino$_{(Cn)}$" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted alkynylamino$_{(C2-C10)}$ has 2 to 10 carbon atoms. The term "heteroatom-unsubstituted alkynylamino$_{(Cn)}$" includes groups, having the structure NHR, in which R is a heteroatom-unsubstituted alkynyl$_{(Cn)}$, as that term is defined above. The term "heteroatom-substituted alkynylamino$_{(Cn)}$" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkynylamino$_{(C2-C10)}$ has 2 to 10 carbon atoms. The term "heteroatom-substituted alkynylamino$_{(Cn)}$" includes groups, having the structure —NHR, in which R is a heteroatom-substituted alkynyl$_{(Cn)}$, as that term is defined above.

The term "arylamino" includes heteroatom-unsubstituted arylamino, heteroatom-substituted arylamino, heteroatom-unsubstituted arylamino$_{(C_n)}$, heteroatom-substituted arylamino$_{(C_n)}$, heteroarylamino, heterocyclic arylamino, and alkyl(aryl)amino groups. The term "heteroatom-unsubstituted arylamino$_{(C_n)}$" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted arylamino$_{(C6-C10)}$ has 6 to 10 carbon atoms. The term "heteroatom-unsubstituted arylamino$_{(C_n)}$" includes groups, having the structure —NHR, in which R is a heteroatom-unsubstituted aryl$_{(C_n)}$, as that term is defined above. The term "heteroatom-substituted arylamino$_{(C_n)}$" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted arylamino$_{(C6-C10)}$ has 6 to 10 carbon atoms. The term "heteroatom-substituted arylamino$_{(C_n)}$" includes groups, having the structure —NHR, in which R is a heteroatom-substituted aryl$_{(C_n)}$, as that term is defined above.

The term "aralkylamino" includes heteroatom-unsubstituted aralkylamino, heteroatom-substituted aralkylamino, heteroatom-unsubstituted aralkylamino$_{(C_n)}$, heteroatom-substituted aralkylamino$_{(C_n)}$, heteroaralkylamino, heterocyclic aralkylamino groups, and diaralkylamino groups. The term "heteroatom-unsubstituted aralkylamino$_{(C_n)}$" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted aralkylamino$_{(C7-C10)}$ has 7 to 10 carbon atoms. The term "heteroatom-unsubstituted aralkylamino$_{(C_n)}$" includes groups, having the structure NHR, in which R is a heteroatom-unsubstituted aralkyl$_{(C_n)}$, as that term is defined above. The term "heteroatom-substituted aralkylamino$_{(C_n)}$" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted aralkylamino$_{(C7-C10)}$ has 7 to 10 carbon atoms. The term "heteroatom-substituted aralkylamino$_{(C_n)}$" includes groups, having the structure —NHR, in which R is a heteroatom-substituted aralkyl$_{(C_n)}$, as that term is defined above.

The term "amido" includes straight-chain amido, branched-chain amido, cycloamido, cyclic amido, heteroatom-unsubstituted amido, heteroatom-substituted amido, heteroatom-unsubstituted amido$_{(C_n)}$, heteroatom-substituted amido$_{(C_n)}$, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted amido$_{(C_n)}$" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted amido$_{(C1-C10)}$ has 1 to 10 carbon atoms. The term "heteroatom-unsubstituted amido$_{(C_n)}$" includes groups, having the structure —NHR, in which R is a heteroatom-unsubstituted acyl$_{(C_n)}$, as that term is defined above. The group, —NHC(O)CH$_3$, is a non-limiting example of a heteroatom-unsubstituted amido group. The term "heteroatom-substituted amido$_{(C_n)}$" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted amido$_{(C1-C10)}$ has 1 to 10 carbon atoms. The term "heteroatom-substituted amido$_{(C_n)}$" includes groups, having the structure —NHR, in which R is a heteroatom-unsubstituted acyl$_{(C_n)}$, as that term is defined above. The group, —NHCO$_2$CH$_3$, is a non-limiting example of a heteroatom-substituted amido group.

As used herein, a "chiral auxiliary" refers to a removable chiral group that is capable of influencing the stereoselectivity of a reaction. Persons of skill in the art are familiar with such compounds, and many are commercially available.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use,* 2002), which is incorporated herein by reference.

An "isomer" of a first compound is a separate compound in which each molecule contains the same constituent atoms as the first compound, but where the configuration of those atoms in three dimensions differs.

A "stereoisomer" is an isomer in which the same atoms are bonded to the same other atoms, but where the configuration of those atoms in three dimensions differs.

"Enantiomers" are stereoisomers that are mirror images of each other, like left and right hands.

"Diastereomers" are stereoisomers that are not enantiomers.

II. Sources of Stem Cells

Various types of stem cells may be used in certain aspects of the present invention for directed neural differentiation or dopaminergic neuron preparation. The term "stem cell" refers to a cell capable of giving rise to at least two different cell types, including pluripotent stem cells and multipotent stem cells. The term "pluripotent stem cell" refers to a cell capable of giving rise to cells of all three germinal layers, that is, endoderm, mesoderm and ectoderm. Although in theory a pluripotent cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming differentiated cells. In certain embodiments, the pluripotent stem cell is an embryonic stem cell derived by somatic cell nuclear transfer.

Neural stem cells can also be used in certain aspects of the present invention. A "neural stem cell" is an undifferentiated cell from neural tissue that is capable of giving rise to more neural stem cells (i.e., exhibits self renewal) and to progeny cells that will terminally differentiate into neural cells. The neural stem cell can be an adult or embryonic neural stem cell.

In certain embodiments of the present invention, pluripotent stem cells and neural stem cells are exposed in vitro to a neural differentiation agent, resulting in the differentiation of the stem cells into neural precursor cells. A neural precursor cell is a cell that can generate neuronal cells (i.e. neurons or neuronal precursors) and glial cells (i.e., astrocytes, oligodendrocytes, or glial cell precursors), but cannot give rise to a pluripotent or neural stem cell.

A. Mammalian Embryonic Stem Cells

Mammalian embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

Depending on culture conditions, ES cells can produce colonies of differentiated cells or undifferentiated cells. The term "differentiate" means the progression of a cell down a developmental pathway. The term "differentiated" is a relative term describing a cell=s progression down a developmental pathway in comparison with another cell. For example, a pluripotent cell can give rise to any cell of the body, while a more differentiated cell such a hematopoetic cell will give rise to fewer cell types. As used herein, "undifferentiated ES cells" refers to ES cells that do not show the characteristics of more specialized cells.

Mouse and human ES cells can be maintained in an undifferentiated state by culturing the cells in the presence of serum and a feeder layer, typically mouse embryonic fibroblasts. Other methods for maintaining ES cells in an undifferentiated state are also known. For example, mouse ES cells can be maintained in an undifferentiated state by culturing in the presence of LIF without a feeder layer. However, unlike mouse ES cells, human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel or laminin, without a feeder layer and in the presence of fibroblast-conditioned medium plus basic fibroblast growth factor, (Xu et al., 2001; U.S. Pat. No. 6,833,269).

The pluripotency of ES cells has been determined in various ways (Martin, 1982). In one test, mouse ES cells derived from the inner cell mass of a blastocyst are injected into the cavity of another blastocyst. The injected blastocyst is deposited into the uterus of a pseudopregnant female mouse to produce progeny that are chimeras of injected and recipient blastocyst cells. In another test, mouse ES cells are injected into adult mice to produce tumors called teratomas. Such tumors can contain a variety of cell types derived from endoderm, mesoderm, and ectoderm. In certain embodiments, one or more teratoma-derived cells may be cultured or differentiated into neuronal or neuronal-committed cells according to the present invention. The pluripotency of human ES cells can also be tested by the formation of teratomas in immunodeficient mice. A third test is to alter culture conditions to allow ES cells to differentiate into more specialized cells. For example, mouse ES cells can spontaneously differentiate into various cell types by removing the feeder layer and adding LIF to the culture medium. Similarly, human ES cells can spontaneously differentiate by removing the feeder layer and growing the ES cells on a non-adherent surface in suspension (Itskovitz-Eldor et al., 2000; Reubinoff et al., 2000; Roach et al., 1993). Under such conditions, the ES cells can form cell aggregates called embryoid bodies which contain cells having characteristics of neurons and heart muscle cells. In all of these tests, the pluripotency of ES cells is shown by their ability to generate cells of endoderm, mesoderm, and ectoderm origin.

Cultures of ES cells are described as "undifferentiated" when a substantial proportion of stem cells and their derivatives in the population display morphological characteristics of undifferentiated cells, clearly distinguishing them from differentiated cells of embryo or adult origin. Undifferentiated ES cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

ES cells can be characterized by the proteins they produce. For example, the following marker proteins have been used to characterize ES cells: stage-specific embryonic antigen SSEA-1, stage-specific embryonic antigen SSEA-3, stage-specific embryonic antigen SSEA-4, tumor rejection antigen-160 (TRA160), tumor rejection antigen-181 (TRA181), alkaline phosphatase (AP), and transcription factor Oct-4. As shown in Table 1, mouse, human and primate cells differ in their pattern of expression of these markers. For example, SSEA-1 is expressed in mouse ES cells, but not human or monkey ES cells, while TRA160 is expressed in human and monkey ES cells but not mouse ES cells.

TABLE 1

ES Cell Marker Expression

| Marker | Mouse | Human | Monkey |
|---|---|---|---|
| SSEA-1 | Yes | No | No |
| SSEA-2 | No | Yes | Yes |
| SSEA-3 | No | Yes | Yes |
| TRA 160 | No | Yes | Yes |
| TRA 181 | No | Yes | Yes |
| Alkaline phosphatase | Yes | Yes | Yes |
| Oct-4 | Yes | Yes | Yes |

Methods for preparing and culturing ES cells can be found in standard textbooks and reviews in cell biology, tissue culture, and embryology, including Teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference.

Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct3/4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF. Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007, doi:10.1038/nature06357). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

D. Neural Stem Cells

Neural stem cells are undifferentiated cells from neural tissue that are capable of giving rise to neural stem cells (capable of self-renewal) or to cells that will terminally differentiate into neural cells. A neural stem cell can be an adult neural stem cell or an embryonic neural stem cell. As used herein, the term "adult" neural stem cell refers to stem cells derived from somatic tissue whether from an adult or a child.

Methods for isolating adult and embryonic neural stem cells from humans and other animals are well known (Rietze and Reynolds, 2006; Svendsen et al., 1999).

III. Dopaminergic Differentiation of Stem Cells

In accordance with the present invention, exposure of stem cells such as neural precursor cells, pluripotent stem cells or neural stem cells in vitro to a dopaminergic differentiation agent of structure (I) results in the formation of dopaminergic neurons. To prepare dopaminergic neurons, the stem cells can be cultured for a time in the presence of the dopaminergic differentiation agent, which could be followed by proliferation in the presence or absence of the dopaminergic differentiation agent.

Variations of this basic procedure are contemplated so long as the result of exposure to the dopaminergic differentiation agent is the differentiation of stem cells to dopaminergic neurons.

For example, stem cells can be cultured in an adherent culture (e.g., plated on a feeder cell) or in suspension on a non-adherent surface in the presence of the dopaminergic differentiation agent. In a second step, after exposure of the stem cells to the dopaminergic differentiation agent for an appropriate amount time, the cells can be cultured in an adherent culture or in suspension on a non-adherent surface in the presence of the dopaminergic differentiation agent, with fresh culture medium. In an optional third step, the exposed cells can be plated and grown in the absence of the dopaminergic differentiation agent. Proliferating cells can be split and passaged when the cells reach about 80-90% confluency.

In the first step, the culture medium can be any medium that supports the survival and growth of pluripotent stem cells or neural stem cells. For example, the culture medium can be DMEM, RPMI 1640, GMEM, or neurobasal medium. The culture medium can contain serum, or can be a serum-free medium. The serum-free medium can be used without the addition of an exogenous growth factor, or can be supplemented with a growth factor such as basic fibroblast growth factor (bFGF), insulin-like growth factor-2 (IGF-2), epidermal growth factor (EGF), fibroblast growth factor 8 (FGF8), Sonic hedgehog (Shh), brain derived neurotrophic factor (BDNF), glial cell line-derived neurotrophic factor (GDNF), or Vitamin C. The non-adherent surface can be low-attachment tissue culture plastic.

As in the first step, the culture medium of the second step can be any medium that supports the growth of pluripotent stem cells or neural stem cells. The medium can contain serum, or can be a serum-free medium with or without the addition of a growth factor. Similarly, the cells can be grown in suspension on a non-adherent tissue culture surface.

In the optional third step, exposed cells can be cultured in suspension or plated on an adherent surface in culture medium containing serum, in serum-free culture medium without a growth factor, or in serum-free culture medium containing a growth factor such as bFGF, IGF-2, EGF, FGF8, Shh, BDNF, GDNF, or Vitamin C.

An adherent surface can be tissue culture plastic, or can be a coated tissue culture surface such as a tissue culture plate coated with polyornithine/laminin, bovine collagen I, human extracellular extract, porcine skin gelatin or Matrigel. Cells can be passaged when they reach confluency, 80-90% confluency, or at any other level of confluency. Either aggregates of cells, single cell suspensions, or both, can be plated. To prepare cells for passaging, cells can be mechanically removed from adherent surfaces, for example by pipetting, or chemically removed by treatment with a protease such as trypsin-EDTA, collagenase or dispase.

All possible combinations of the first, second and third steps are contemplated. For example, in one procedure, the first step involves the use of serum-free medium without a growth factor, while the second and third steps involve the use of serum-free medium with a growth factor. In another procedure, all three steps involve the use of serum-free medium with a growth factor. In other procedures, the first and second steps are combined such that cells are exposed to the dopaminergic differentiation agent without a change in culture medium before being plated in the third step.

Effective concentrations of a dopaminergic differentiation agent can be determined by a dose-response analysis. The dopaminergic differentiation agent can be dissolved in a solvent such as dimethyl sulfoxide (DMSO), then added at various concentrations to ES cell cultures. The extent of differentiation of ES cell cultures after exposure to different amounts of the dopaminergic differentiation agent can be determined by measuring the expression of promoters, genes and proteins active in dopaminergic neural cells and/or neuronal cells. For example, expression of neural markers such as the Tα-1 promoter, the β3-tubulin gene and protein, the nestin gene and protein, the doublecortin gene and protein, the vimentin gene and protein, the NeuN gene and protein, or the MAP2 gene and protein or dopaminergic markers such as tyrosine hydroxylase (TH) gene and protein and dopaminergic transporter (DAT) gene and protein can be analyzed. A typical range of concentrations for the dose-response analysis are 100 nM to 100 mM of the dopaminergic differentiation agent.

Differentiated cells or a cell population comprising dopaminergic neurons prepared by exposure of undifferentiated stem cells, neural stem cells, or neural precursors to the dopaminergic differentiation agent can be characterized morphologically, immunochemically and in other ways to confirm their status as dopaminergic neural cells.

IV. Dopaminergic Neurons and Disorders Thereof

Dopaminergic neurons may be prepared by the foregoing methods of the present invention and may be used for treatment of neurological disorders or neurotoxicity testing. "Dopaminergic neurons" used herein refers to neuronal cells that produce the neurotransmitter dopamine. Preferably dopaminergic neurons secrete the neurotransmitter dopamine, and have little or no expression of dopamine-β-hydroxylase. Dopamine, along with epinephrine, norepinephrine, and serotonin, belongs to a chemical family referred to "monoamines." Within the family of monoamines, epinephrine, norepinephrine, and dopamine are derived from the amino acid tyrosine and form a subfamily called the catecholamines. Frequently, tyrosine hydroxylase (TH), the rate-limiting enzyme for the biosynthesis of dopamine, is used as a marker to identify dopaminergic neurons.

Dopaminergic neurons in vivo innervate the striatum, limbic system, and neocortex, and reside in the ventral midbrain together with several other classes of neurons including motor neurons. Dopaminergic neurons are specifically located in the substantia nigra of midbrain, and control postural reflexes, movement, and reward-associated behaviors.

Neural cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Certain cells embodied in this invention have morphological features characteristic of neuronal cells or dopaminergic neural cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells. Markers of interest include but are not limited to: a) β3-tubulin, microtubule-associated protein 2 (MAP-2), or neurofilament, characteristic of neurons; b) glial fibrillary acidic protein (GFAP), present in astrocytes; c) 2', 3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax 6 and nestin, characteristic of neural precursors and other cells; f) Sox 1, characteristic of developing central nervous system; g) tyrosine hydroxylase (TH), present in dopaminergic neurons; h) glutamic acid decarboxylase, isoform 67 (GAD67), present in neurons containing gamma-aminobutyric acid; and i) vimentin, characteristic of intermediate neuronal differentiation.

Tissue-specific markers listed in this disclosure and known in the art can be detected using any suitable immunological technique, such as flow immunocytochemistry and fluorescence activated cell sorting for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Antibody binding to an antigen can be observed by standard immunocytochemistry or flow cytometry assay, after fixation of the cells, using a labeled secondary antibody or other conjugate (such as a biotin-avidin conjugate) to amplify labeling, or other immunological methods well known in the art. In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277, 437; 4,275,149 and 4,366,241, each incorporated herein by reference.

The expression of tissue-specific gene products can also be detected at the mRNA level by Northern blot analysis or dot-blot hybridization analysis, or by reverse transcriptase initiated polymerase chain reaction (RT-PCR) using sequence-specific primers in standard amplification methods which are described in detail in U.S. Pat. Nos. 4,683,195, 4,683,202 and 4,800,159, and in Innis et al., 1988, each of which is incorporated herein by reference in their entirety. Sequence data for the particular markers listed in this disclosure can be obtained from public databases, such as GenBANK. Expression of tissue-specific markers as detected at the protein or mRNA level is considered positive if the level is at least 2-fold, and preferably more than 10- or 50-fold above that of a control cell, such as an undifferentiated ES cell.

Also characteristic of neural cells, particularly terminally differentiated cells like dopaminergic neurons, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

In certain aspects, the present invention provides a method of preparing dopaminergic neuronal cells in vitro by exposing stem cells to the dopaminergic differentiation agent of structure (I). Under appropriate conditions, the exposed cells differentiate into dopaminergic neurons. Differentiation into dopaminergic neuronal cells can be determined by the morphology of the differentiated cells, the expression of dopaminergic markers in the differentiated cells, and the electrophysiological functioning of differentiated neuronal cells.

V. Methods for Screening Test Compounds and Assessing Toxicity

Certain aspects of the present invention further comprise methods for evaluating the toxicity of a test compound in dopaminergic neural cells which have been prepared, cultured and/or differentiated according to the present invention. These assays may comprise testing a single test compound or random screening of large libraries of candidate substances; alternatively, the assays may be used to focus on particular classes of compounds selected with an eye towards structural attributes that are believed to make them more likely to modulate the function of neurons or neuronally-committed cells, particularly dopaminergic neurons.

In certain embodiments, the toxicity of a test compound may be evaluated by contacting the compound with a plurality of neuronal or neuronally-committed cells comprising dopaminergic neural cells, such as cells which have formed into an engineered neural tissue (ENTs) (e.g., derived from human embryonic stem cells). ENTs are 3-dimensional pieces of tissues derived from embryonic stem cells (ES) which resemble certain layers of human fetal brain which may be produced via the differentiation of cells according to the present invention. The toxicity testing may be utilized as a part of an in vitro drug-screening process, e.g., prior to the clinical administration of the test compound to a subject, such as a human patient.

Various attributes may be evaluated to determine if a test compound results in toxicity in cells of the central nervous system. Parameters including, for example, cell death (necrosis, apoptosis), excitotoxicity, cytotoxicity, altered neuronal function (e.g., altered generation of action potentials or long-term potentiation, etc.), altered brain receptor function, decreased resistance to challenge with a known toxic compound, synaptic toxicity, developmental neurotoxicity, or neural lineagespecific toxicity (e.g., in oligodendrocytes, astrocytes, or dopaminergic neurons) may be assessed in the cells to determine if a test compound results in toxicity or neurotoxicity. Electrophysiological techniques may be used to detect neuronal activity or function. Measure of synaptic markers may be used to detect compounds with a synaptic toxicity.

Cells may be engineered to contain a promoter specific for a defined lineage (e.g., dopaminergic neurons) controlling the expression a reporter gene, such as a luminescent or fluorescent protein; in this way, neural lineagespecific toxicities may be more easily observed by changes in the expression of the reporter gene in vitro. In certain embodiments, reactive oxygen species may be measured to determine if a test compound results in increased cellular oxidative stress. In certain embodiments, dose-response relationships may be generated to assess the toxicity of a test compound. In certain embodiments, developmental neurotoxicity may be assessed by incubating a test compound with cells during neural differentiation. In further embodiments, chronic neurotoxicity may be assessed by incubating a test compound with cells for an extended period, such as at least or about 1, 2, 3, 4, 5, 6, 7, 8, 9, 10, 12 weeks or any range derivable therein.

Multiple compounds or part or all of a small molecule library may be screened for toxicity or neuronal activity in cells cultured or prepared according to the present invention. In particular, some or essentially all of the neuronal or neuronal-committed cells may be differentiated into dopaminergic neural cells according to certain aspects of the present methods prior to the assessment of the toxicity of a test compound; this may be particularly useful in instances where it may be desirable to understand the dopaminergic toxicity of a compound.

The culturing and/or toxicity testing methods of the present invention may be automated. In certain embodiments, one or more of the steps involved with culturing cells, differentiating cells, and/or evaluating the a property (e.g., the toxicity) of a test compound may be automated, e.g., via the use of robotics, to facilitate high-throughput toxicity assessment in cells. For example, various robotics may be used to culture cells, add or remove media from the cells, add a test compound to media comprising neuronal or neuronally-committed cells differentiated according to the present invention. Specific robotics which may be used with the methods of the present invention include cell dispensers that allow automated and standardized distribution of cells in multiwells which typically range from 12 to 384 wells although a higher or lower number of wells can be used as desired (e.g., Matrix WellMate™ from Thermo Fisher Scientific, Inc.) and multichannel liquid handlers that allow automated distribution of library compounds into multiwell plates and automated dilutions of compounds, e.g., for $IC_{50}$ calculations (e.g., Zephyr from Caliper Life Sciences).

To assess the toxicity of a compound, one generally may determine the function and/or viability of cells in the presence and absence of the test compound. For example, a method generally comprises:

providing a test compound;

admixing the test compound with an isolated cell, plurality of cells, or one or more ENTs which have been prepared, cultured and/or differentiated according to the present invention;

measuring whether or not the candidate modulator can alter or disrupt cell viability or function in the cell or cells in step (c); and comparing the characteristic measured in step (c) with the characteristic of the control cell, cells, or ENTs in the absence of said candidate modulator, wherein a difference between the measured characteristics indicates that said candidate modulator affects or exhibits toxicity against the cell or cells.

Screening may be carried out in a high-throughput assay using one or more multi-well plates, such as a 96 well plate. For example, ENTs may be produced in multi-well plates in order to establish a screening platforms to study the neurotoxic potential of a test compound (e.g., a small molecule, protein, peptide, antibody, putative therapeutic) or multiple compounds (e.g., from a compound bank, small molecule library, peptide library, antibody library, etc.). Test compounds may be synthetically produced or purified from natural sources. Methods for producing ENTs and/or evaluating the properties of a test compound may be automated; for example, steps of adding or removing a compound or solution to a multi-well plate, detecting luminescence or fluorescence in a multi-well plate, and/or producing ENTs in a multi-well plate may be automated, e.g., via robotics.

In various embodiments, combinations of test compounds may be evaluated to determine if the simultaneous or sequential application of 2, 3, 4, 5, 6, or more test compounds to a neural or neuronally-committed tissue results in a particular effect or toxicity. The sequential administration of multiple compounds to a tissue may vary from seconds to hours, weeks, or longer, as desired. For example, in such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Various combinations may be employed between test compound "A" and test compound "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | | B/B/A/A | |
| B/A/B/A | B/A/A/B | A/A/A/B | B/A/A/A | A/B/A/A | | A/A/B/A | |

In other embodiments, test compounds may be separately contacted with different neural or neuronally-committed tissue(s).

Because neural differentiation agents of the present invention, such as phenazopyridine, or dopaminergic differentiation agents such as zoxazolamine, can promote ENTs formation, resulting ENTs may be tested for toxicity and may serve as a suitable in vitro model for toxicity testing on the human brain. The complex networks of neurons typically present in ENTs can resemble the human fetal brain in many aspects and thus may represent a more accurate model of the human brain which may be used for in vitro testing, such as evaluation of the neurotoxicity of a test compound. These methods may be a particularly tool for industry and drug development and/or for screening compounds for possible neurotoxicity.

Compounds of the present invention, such as phenazopyridine, can also improve the quality of ENTs and decrease the occurrence of contaminating non-neural tissues. As shown in further detail in the Examples, phenazopyridine and/or zoxazolamine have been used by the inventors to produce ENTs. These methods may be utilized in large scale ENT production.

In certain embodiments ENTs may be engineered to include a neural-specific promoter coupled to a luminescent or fluorescent protein (e.g., GFP, eGFP, EBFP, EBFP2, Azurite, mKalama1, ECFP, Cerulean, CyPet, YFP, Citrine, Venus, YPet, Firefly luciferase, *Renilla* luciferase). In this way, the cellular identity and viability may be optically detected, e.g., via a microscope and/or automated optical detection method (e.g., fluorescent activated cell sorting or FACS). In the presence of a neurotoxic compound, decreased expression or of the luminescent protein in culture, such as an ENT, could be used to identify the death of neuronal or neuronally committed cells. Thus, as compared to a control tissue, increases or decreases in expression of a marker or "tag" protein (e.g., a spectrophotometrically detectable or enzymatic protein) may be used to identify compounds which promote or reduce neuronal survival.

Specific neuronal promoters which may be used for this purpose include, for example, the Tα1 α-tubulin promoter (Tα1) and the βIII-tubulin promoter. Various promoters for specific neuronal lineages may be used to evaluate responses in specific cell types, including, e.g., dopaminergic neuron-specific promoters (e.g., tyrosine hydroxylase promoter), synapse-specific promoters (e.g., synapsin I promoter), axon-specific promoters (e.g., MAP2 promoter), and non-neuronal-specific promoters (e.g., oligodendrocytes assessed by CNPase II promoter). The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

In certain embodiments a pluripotent stem cell may be transfected with a dual reporter system to detect differentiation of the stem cell into a neuronal or neuronally-committed cell. The dual reporter system may utilize a neuron-specific promoter to express a first luminescent or fluorescent protein and a second promoter (e.g., a promoter expressed by all cells or by a second cell type such as a dopaminergic promoter) can drive the expression of a second luminescent or fluorescent protein. In this way, the relative expression of neuronal markers may be observed. A reporter system may be transfected into a pluripotent cell via a variety of techniques including, e.g., liposomal transfection, microparticle bombardment, or viral transfection such as lentiviral transfection.

Fluorescent proteins generally comprise a fluorescent chromophore, the chromophore being formed from at least 3 amino acids and typically characterized by a cyclization reaction creating a p-hydroxybenzylidene-imidazolidinone chromophore. The chromophore may not contain a prosthetic group and is capable of emitting light of selective energy, the energy having been stored in the chromophore by previous illumination from an outside light source comprising the correct wavelength(s). Spontaneously fluorescent proteins can vary widely in structure and the number of amino acids present in a chromophore, provided that the chromophore comprises the p-hydroxybenzylidene-imidazolidinone ring structure. In some instances, a fluorescent protein may comprise a β-barrel structure such as that found in green fluorescent proteins and described in Chalfie et al. (1994). Fluorescent proteins typically exhibit the ability to emit, in response to an incident light of a particular wavelength absorbed by the protein, a light of longer wavelength. Fluorescent activated cell sorting or (FACS) may be used to detect the expression of one or more neuron-specific markers in certain embodiments. FACS products are available, e.g., FACSCalibur™ (Becton Dickson) which may be used with the present invention.

Test compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other test compounds include antisense molecules, ribozymes, and antibodies (including single chain antibodies), each of which would be specific for the target molecule. For example, an antisense molecule that bound to a translational or transcriptional start site, or splice junctions, would be ideal candidate inhibitors. Peptidomimetics of peptide modulators or other compounds which are sterically similar to pharmacologically active compounds may also serve as test compounds.

It will, of course, be understood that all the screening methods of the present invention are useful in themselves notwithstanding the fact that toxicity or some other property may or may not be observed in a test compound.

VI. Treatment of Dopaminergic Disorders

In another aspect, the present invention provides a method of treating dopaminergic disorders, comprising administering to a subject in need of such treatment an effective amount of dopaminergic differentiation agent or a cell population comprising dopaminergic neurons in accordance with the present invention.

A. Dopaminergic Disorders

The dopaminergic disorders may be any disorder having a loss of function or number of dopaminergic neurons, including a reduction in normal function or number of dopaminergic neurons. In essence, the dopaminergic differentiation agent such as the substituted benzoxazole of the present invention can be used to treat any dopaminergic disorder that results from loss or injury of neural or dopaminergic neural cells. For example, the loss of normal functional dopaminergic neurons may result in Parkinson's disease, and their abnormal function could be associated with schizophrenia and drug addiction.

Parkinson's disease (PD) is characterized by the progressive loss in function of dopaminergic neurons. The progressive loss of dopaminergic function interferes with the normal working of the neuronal circuitry necessary for motor control so that patients with PD show characteristic motor disturbances such as akinesia, rigidity and rest tremor. Other symptoms include pain, impaired olfaction, alterations of personality and depression. Quinn et al., (1997) Baillieres Clin. Neurol. 6:1-13.

The dopaminergic disorders can be also due to any neural loss, neurodegenerative disorder or nervous system injury. Neurodegenerative disorders include diseases such as Alzheimer's disease, frontotemporal dementia, dementia with Lewy bodies, amyotrophic lateral sclerosis (Lou Gehrig's disease), Parkinson's disease, Huntington's disease and multiple sclerosis. Nervous system injury includes injury due to ischemic cerebral stroke, spinal cord lesions, brain injury, post-hypovolemic and hypotensive brain damage (including post-operative brain damage), post-infectious complications (including post-meningitis hypocampus degeneration, brain parenchyma damage after abcesses and herpes simplex encephalitis).

According to the invention, dopaminergic neuronal cells are generated using the cell culturing method described above. A cell population comprising the dopaminergic neural cells may be then administered to the brain of the patient in need thereof to produce dopamine and restore behavioral deficits in the patient. Preferably, the cells are administered to the basal ganglia of the patient. In another embodiment, the dopaminergic differentiation agent may be administered to the patient for treatment of dopaminergic neuron disorders by generation of dopaminergic neurons in vivo.

B. Pharmaceutical Formulations and Administration of a Dopaminergic Differentiation Agent With regard to treatment of a patient, an "effective amount" of a dopaminergic differentiation agent such as a substituted benzoxazole of the present invention, or a pharmaceutical composition containing a dopaminergic differentiation agent of the present invention, is an amount sufficient to produce newly formed neural cells, more specifically, dopaminergic neural cells, in the damaged region of the nervous system.

During treatment, stem cells such as adult neural stem cells are exposed to the administered dopaminergic differentiation agent. The dopaminergic differentiation agent can act in various ways on the adult neural stem cells. For example, the dopaminergic differentiation agent can act on the adult neural stem cells located in a patient's nervous system to cause differentiation of the adult neural stem cells into dopaminergic neural cells. In some embodiments, the dopaminergic differentiation agent can stimulate the proliferation of adult neural stem cells, dopaminergic neural cells, radial glial cells, neuroepithelial cells or other neural precursor cells. Similar actions have been proposed for other factors that enhance the proliferation and differentiation of neural cells, such as interferon gamma (Kim et al., 2007), leukemia inhibitory factor (Bauer et al., 2006), TGF-alpha (Fallon et al., 2000). By enhancing proliferation and/or differentiation of neural cells in the damaged area of the nervous system, the treatments of the present invention may lead to regeneration of dopaminergic neurons and recovery of nervous system function.

Pharmaceutical compositions and formulations of the dopaminergic differentiation agent can be administered by direct injection into damaged areas of the nervous system, or administered parenterally, intravenously, intradermally, intramuscularly, transdermally, intraperitoneally, intrathecally, or per os.

For injection, solutions of the active compounds as free base or pharmacologically acceptable salts can be prepared, for example, in water, glycerol, liquid polyethylene glycols, and mixtures thereof and in oils, to form a solution or suspension. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions may be administered in a manner compatible with the dosage formulation and in such amount as is therapeutically effective. The formulations are easily administered in a variety of dosage forms such as injectable solutions, drug release capsules and the like. Methods of preparing formulations will be apparent to those skilled in the art (for example, see Remington's Pharmaceutical Sciences" 15th Edition).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared For treatment of a dopaminergic disorder such as nervous system damage, in certain aspects, adult neural stem cells may be exposed to a dopaminergic differentiation agent of the present invention. The routes of administration may vary, naturally, with the location and nature of the damage, and include, e.g., intradermal, transdermal, parenteral, intravenous, intramuscular, intranasal, subcutaneous, percutaneous, intratracheal, intraperitoneal, perfusion, lavage, direct injection, and oral administration and formulation.

The dopaminergic differentiation agent can be given in a single dose, or multiple doses. Continuous administration also may be applied where appropriate. The dose of a therapeutic composition via continuous perfusion may be equivalent to that given by a single or multiple injections, adjusted over a period of time during which the perfusion occurs. The amount of dopaminergic differentiation agent administered may be dependent on the subject being treated, the subject's weight, the manner of administration, and the judgment of the physician. Treatment regimens may vary as well, and often depend on the type of nervous system damage, location of the damage, disease progression, and health and age of the patient.

In some embodiments, a dopaminergic differentiation agent of the present invention is administered to a patient systemically or by local injection. Systemic administration can be by intravenous or intraperitoneal delivery. The dopaminergic differentiation agent can be administered to reach a circulating level of about 2 to 20 mg/ml in blood, or a dose of about 100-300 mg can be delivered to a patient.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

C. Cell Formulations and Administration

After the differentiated neuronal cells are formed according to the cell culturing method previously described, the cells may be suspended in a physiologically compatible carrier. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, and Hank's balanced salt solution+/−glucose (HBSS).

The volume of cell suspension administered to a patient may vary depending on the site of implantation, treatment goal and amount of cells in solution. The amount of cells administered to a patient may be a "therapeutically effective amount." As used herein, a therapeutically effective amount refers to the number of transplanted cells which are required to effect treatment of the particular disorder. For example, where the treatment is for Parkinson's disease, transplantation of a therapeutically effective amount of cells may produce a reduction in the amount and/or severity of the symptoms associated with that disorder, e.g., rigidity, akinesia and gait disorder.

It is estimated that a severe Parkinson's patient will need at least about 100,000 surviving dopamine cells per grafted side to have a substantial beneficial effect from the transplantation. As cell survival is low in brain tissue transplantation in general (5-10%) an estimated 1-4 million dopaminergic neurons should be transplanted.

According to certain aspects of the invention, the cells are administered to the patient's brain. The cells may be implanted within the parenchyma of the brain, in the space containing cerebrospinal fluids, such as the sub-arachnoid space or ventricles, or extraneurally. As used herein, the term "extraneurally" is intended to indicate regions of the patient which are not within the central nervous system or peripheral nervous system, such as the celiac ganglion or sciatic nerve. "Central nervous system" is meant to include all structures within the dura mater.

Typically, the neuronal cells are administered by injection into the brain of the patient. Injections can generally be made with a sterilized syringe having an 18-21 gauge needle. Although the exact size needle may depend on the species being treated, the needle should not be bigger than 1 mm diameter in any species. Those of skill in the art are familiar with techniques for administering cells to the brain of a patient.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Zoxazolamine for Dopaminergic Differentiation

The inventors identified a small molecule zoxazolamine that can promote the differentiation of mouse embryonic stem cells (CGR8 line) into dopaminergic neurons. For example, this molecule can serve in the future as a candidate for ES-derived cells for Parkinson's disease therapy. CGR8 cells were seeded on irradiated PA6 monolayer at the density of 60 cells per well in 96-well (cell culture plates) and zoxazolamine was added to the cells after 24 hours of plating at a final concentration of 10 µm. Cells were differentiated into dopaminergic neurons in 16 days. The dopaminergic differentiation was performed under the gold standard condition as described below in the presence or absence of zoxazolamine. The dopaminergic neurons was quantified by radioligand [$^3$H] Win 35,428 binding as described below. The triplicate signals of enhancement of dopaminergic differentiation by zoxazolamine confirmed the reproducibility and the validity of the dopaminergic differentiation effect.

Example 2

Gold Standard Condition for Dopaminergic Differentiation

The inventors developed a gold standard for mouse embryonic stem cells (CGR8 line) differentiation into dopaminergic neurons in the presence of small organic compounds that favour dopaminergic neuronal differentiation. This gold standard condition permits the generation of maximum amount of dopaminergic neurons. This gold standard is simple, robust and reproducible. The gold standard was based on the co-culture of mouse embryonic stem cells (CGR8 line) on a monolayer of irradiated PA6 feeder cells isolated from skull bone marrow (Barberi et al. 2003). Dopaminergic differentiation by the present method can be performed in a 96 well plate. This method is particularly well suited for in vitro differentiation.

A) Ratio of CGR8/PA6

To determine the optimum ratio of CGR8/PA6 that provides neuronal differentiation in which the presence of dopaminergic neurons is maximum, the inventors compared between different densities of CGR8 line (from 500 to 3000 cells/well in 6 well cell culture plates).

The inventors observed that the optimal ratio was 1000 CGR8/125 000 PA6. 70% of the neurons are βIII-tubulin neurons, among these neurons≈30% neurons were found TH positive, thus suggesting the presence of DA-neurons.

Among these 30%, <5% were neurons DAT positive. This suggested that dopaminergic neurons could be observed at late stage of differentiation and they are very rare.

B) Time of Differentiation

As DAT was the target for readout, the culture conditions to detect this protein were established. To define the optimal duration of CGR8/PA6 co-culture with a very large scare of dopaminergic neurons, mouse embryonic stem cells (CGR8 line) were differentiated for various periods of time from 8 to 16 days of differentiation. The conditions used for cells differentiation into DA-neurons were essentially as described before.

A kinetic of differentiation of mouse embryonic stem cells (CGR8 line) has been done from 8 to 16 days on monolayer of irradiated PA6 stromal cell line. Immunofluorescence analysis confirmed that at 8 days of differentiation, DAT positive neurons have never been observed but, they appeared systematically at 16 days with at least >5% of neurons.

Materials and Methods:

I. Maintenance of Undifferentiated Mouse Embryonic Stem Cells (CGR8 Line)

Undifferentiated mouse embryonic stem cells (CGR8 line) were maintained on gelatin-coated dishes in GMEM (Gibco) supplemented with 2 mM glutamine (Gibco), 1% β-mercaptoethanol (Sigma), 1% non essential amino acids (Gibco), 2,000 units/ml leukemia inhibitory factor (LIF) (Chemicon International), 2% sodium pyruvate (Gibco), 1% penicillin and 1% streptomycin (Gibco), and 10% ES serum (Gibco).

A) Thawing embryonic stem cells, maintenance and passaging (cells storage at −80° C.): 10 ml of propagation medium was placed in coated gelatin dishes and the dishes were put in the incubator; 10 ml of propagation solution was put in a sterile tube; the cells were taken from the freezer and thawed at 37° C.; the thawed cells were put in the tube containing 10 ml of propagation medium, and centrifuged at 1000 rpm for 5 min; the supernatant was removed and the cap was kept; the cap was taken with 10 ml of medium of propagation; LIF 20 µl was added to each dish; the cells were put in the dishes at 37° C. in the incubator B) Passaging Embryonic Stem Cells Cells were passed every 2 days, depending on their confluence by the following steps:

Remove the medium

Wash once with 10 ml of PBS

Trypsinization: Add 0.5% trypsinEDTA (Gibco) to the cells and put them in the incubator; Prepare a gelatine coated dish with 9-10 ml medium; Shake and check the digestion of the cells; Check the dissociation at the microscope, cells must be single (80-90%) and if necessary pipette up and down with 5 ml pipette until 80-90% of the cells are single; Put a fraction of the cells in a new dish with medium; Add 20 µl LIF/10 ml in each dish to the new dish.

At this stage cells can be cultured and expanded indefinitely to store aliquots of undifferentiated cells in liquid nitrogen C) Coating of Petri Dishes with Gelatin Gelatin 0.01% type B (Sigma) were prepared in PBS (Gibco/Invitrogen), each dish were covered with 10 ml (final volume) for 45 min at RT, followed by desiccation for 90 min under the hood.

D) Media Culture

Propagation Medium for Mouse Embryonic Stem Cells (CGR8 Line) Maintenance

| | |
|---|---|
| BHK21 = GMEM (Gibco) | 500 ml |
| Non essential amino acid 100 × (Gibco) | 5 ml |
| Penicillin/streptomycin 100 × (Gibco) | 5 ml |
| L-Glutamine (Sigma) | 5 ml |
| Sodium Pyruvate (Gibco) | 5 ml |
| β-mercaptoethanol (Sigma) | 500 µl |
| Fetal bovine serum for ES culture (Gibco/Invitrogen) | 50 ml |

Propagation Medium for PA6 Cells Maintenance

| | |
|---|---|
| MEM alpha (Gibco) | 500 ml |
| Fetal bovine serum (EU) (Hyclone) | 50 ml |
| Penicillin/streptomycin100 × (Gibco) | 5 ml |

PA6 Differentiation Medium

| | |
|---|---|
| BHK21 = GMEM (Gibco) | 500 ml |
| Non essential amino acid 100 × (Gibco) | 5 ml |
| Penicillin/streptomycin 100 × (Gibco) | 5 ml |
| L-Glutamine (Sigma) | 5 ml |
| β-mercaptoethanol (Sigma) | 500 µl |
| Knockout serum (KO) (Gibco/Invitrogen) | 50 ml |

II. Differentiation of Mouse Embryonic Stem Cells (CGR8 Line)

To induce the differentiation of mouse embryonic stem cells into dopaminergic neurons, cells were differentiated for 16 days, the following steps have been used:

Remove the propagation medium from the CGR8 cells Petri dish

Wash once with 10 ml of PBS

Add 1.5 ml of trypsin-EDTA on the dish containing CGR8 and leave it for 3-5 min at 37° C.

Add 5-7 ml of CGR8 propagation medium and pipette the solution so that the cells are well isolated (no cell clusters should be visible in the solution in the pipette)

Collect the cells in 15 ml tube and centrifuge the tube

Remove the supernatants and resuspend the cells with 1 ml of warm propagation medium (PA6 differentiation medium)

Dilute the cells to 1000 cells/well in 6 well cell culture plates, the dilution should be made in a new 50 ml falcon tube Plating cells on a confluent layer of irradiated PA6 stromal cell line III. Immunofluorescence Microscopy A) Protocol Staining Immunofluorescence was carried out according to standard techniques, in brief; mouse embryonic stem cells (CGR8 line) were grown on glass cover slips coated with PA6 feeder monolayer in six-well plates for 16 days.

Cells were fixed with 2% Paraformaldehyde for 30 min, washed with PBS and permeabilized with 0.5% (v/v) Triton x-100 for 30 min.

The cells were then exposed to primary antibodies overnight at 4° C. The following primary antibodies were used for staining rat anti dopamine transporter (1/1000; Chemicon), rabbit anti βIII-tubulin (1/2000; Covance), mouse anti βIII-tubulin (1/2000; Sigma), mouse anti tyrosine hydroxylase (1/200; Santa Cruz), rabbit anti tyrosine hydroxlase (1/200; Chemicon).

After two washes in PBS, cells were incubated with PBS containing 1% serum (blocking buffer FBS). Then cells were stained with secondary antibodies at RT for 90 min (1:1000 dilutions in blocking buffer).

For the secondary detection, Alexa fluor 488 or 555 conjugates were used. Cell nuclei were stained with 1 µg/ml of 4'-6-Diamidino-2-phenylindol (DAPI) for 10 min. Then cells were washed 3 times for 10 minutes with PBS. The immunofluorescence photographs were taken with a fluorescence microscopy.

B) Solutions

PBS −2% formaldehyde (472 ml Hanks' balanced salt solution (HBSS) (Invitrogen) +28 ml formaldehyde 36%, 4° C.)

PBS −0.2% Triton X-100

PBS −1% Fetal bovine serum (FBS)

IV. RNA Extraction and RT-PCR Analysis

The inventors selected the primer for RT-PCR from published works (Barberi et al. 2003).

Real time PCR was performed on different stages of samples; cells were differentiated from 8 to 16 days in vitro. Total cellular RNA was isolated using Qiagen RNeasy Mini Kit and Qiagen-RNase-Free DNase Set.

The RNA extraction and RT-PCR were performed according to the procedure recommended by the manufacturer of (QIAGEN).

1 µg of total RNA was transcribed into cDNA using Superscript™. Conditions for PCR reactions were optimized by varying $MgCl_2$ concentration and cycle numbers to determine linear amplification range. Amplification products were identified by size and confirmed by DNA sequencing. DAT gene expression values were normalized to those of GADPH.

Example 3

$[^3H]$ Win 35,428 Binding on DAT Receptor and DA Neurons

A compatible system was established to read out and quantify dopaminergic neurons. For this purpose, a competitive assay was developed based on radioligand $[^3H]$ Win 35,428 that is a ligand which binds specifically to dopaminergic transporter DAT. One of the ultimate goals of the binding assay is to confirm if it is possible to label DAT receptor and dopaminergic neurons differentiated from mouse embryonic stem cells (CGR8 line) by using radioligand $[^3H]$ Win 35,428.

$[^3H]$ Win 35,428 has been used on cells purified from central nervous system in vivo. For in vitro experiments, $[^3H]$ Win 35,428 was mainly used on membranes preparation but has never demonstrated in vitro on ESCderived cells.

To facilitate the demonstration of this proof of concept, the inventors decided (i) to validate the proof of concept on 6 well plates (easier), (ii) to adapt the binding, if the results are convincing to 96-well culture plates.

Cells were incubated on binding buffer containing 5 nM of the ligand at different time (30 to 60 minutes), with and without 10 µm of GBR 12909 hydrochloride. GBR 12909 hydrochloride (Sigma) is a specific antagonist of DAT receptor (Valchar et al. 1993), it binds to DAT receptor and inhibited $[^3H]$ Win 35,428. Radioactivity measured by liquid scintillation counter (WALLAC).

Quantitative analysis of radioactivity showed that cells incubated with $[^3H]$ Win 35,428 alone give rise to a signal. A non-specific binding was observed in cells which were incubated with GBR 12909 hydrochloride and it's conformed to 50% of the total binding of $[^3H]$ Win 35,428.

To adapt $[^3H]$ Win 35,428 binding to DAT receptor and DA-neurons in 96-well plate, cells were plated at the density of 60 cells/well.

The differentiation of mouse embryonic stem cells (CGR8 line) has been described above. After 16 days of differentiations, cells were incubated with $[^3H]$ Win35, 428 for 1 hour and then washed by binding buffer for 1 minute, following by direct counting using liquid scintillation counter (WALLAC).

A signal was confirmed in cells incubated with 5 nM of ligand $[^3H]$ Win35, 428 alone and the signal degreased for cells incubated with 10 µm of GBR 12909 hydrochloride, especially at 60 minutes.

In conclusion $[^3H]$ Win 35,428 label specifically dopaminergic neurons in 96 well cell culture plates using this simple and reproducible procedure.

This assay permits quantitative determination of the affinity, abundance, and binding specificity of radioligand $[^3H]$ Win 35,428. In detail, the binding assay was performed at 4° C. in phosphate-buffered saline (PBS) (Invitrogen/Gibco) containing 0.32 M sucrose with $Ca^{2+}$ and $Mg^{2+}$. Cells in each well were washed one time with 0.5 ml of phosphatebuffered. Then incubated at various time (30 to 60 min) with various amounts (5 to 10 nM) of [$^3$H] Win 35,428. The non specific binding was determined in the presence or not of 10 µM of GBR-12909 hydrochloride. The incubation was stopped by rinsing the cells three times with ice-cold buffer to eliminate non-linked [$^3$H] Win 35,428 and removal of cells. Cells were detached by a rake and transferred into a 96 well plate. Radioactivity was measured by a liquid scintillation counter (WALLAC).

Example 4

Zoxazolamine Effect on Neural and Dopaminergic Differentiation

The gold standard conditions used for cells differentiation into DA-neurons were essentially as described before. Mouse ES cells (mouse CGR8 Cells) were subjected to neural differentiation using the PA6 feeder cells, in the presence of DMSO alone as a negative control or in the presence of an appropriate concentration of zoxazolamine. Immunofluorescent staining as described above was used to evaluate, after defined times, the amount of neurons and dopaminergic neurons.

Mouse ESC maintenance and differentiation methods and materials were the same as described in Example 2. The optimal ratio ESC CGR8/PA6 feeder cells in these conditions was 1000/125 000 PA6 in 2 ml differentiation medium containing zoxazolamine. Note that PA6 were initially seeded on a glass coverslip. The optimal concentration of zoxazolamine in these conditions was 2 µM. DMSO was used as the vehicle alone control. Immunofluorescent staining was used to evaluate, after 16 days unless otherwise specified, the amount of neurons and dopaminergic neurons.

As shown in FIG. 1, zoxazolamine increased neuronal maturation of mouse ES cells (ESC). Mouse ESC were submitted to neural differentiation by co-culturing with PA6 as described above, in the presence of 10 µM zoxazolamine. After one week, immunoreactivity against the marker of mature neurons NeuN was assessed and quantified by the Metamorph picture analysis software (Molecular Devices). Zoxazolamine favors the neuronal maturation as seen by the increased absolute number and percentage of mature-stage neurons positive for NeuN.

Figure 2:
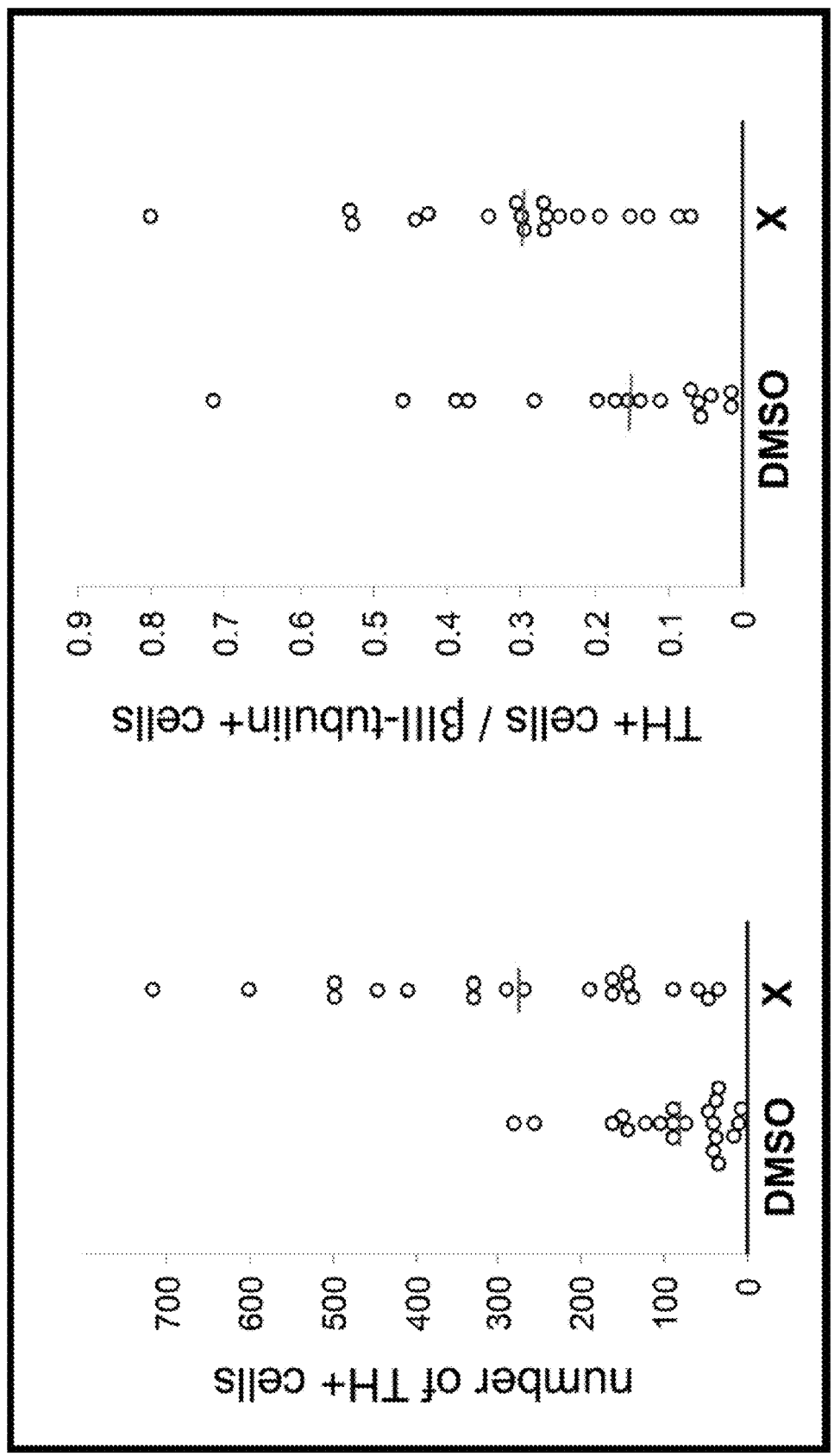
FIG. 2. Zoxazolamine favoured dopaminergic differentiation of mouse ESC.

As shown in FIG. 2, zoxazolamine favoured dopaminergic differentiation of mouse ESC. Mouse ESC were submitted to neural differentiation by coculture with PA6 as described above, in the presence of 10 µM zoxazolamine. After one week, immunoreactivity against the marker of dopaminergic neurons Tyrosine Hydroxylase (TH) was assessed and quantified by the Metamorph picture analysis software (Molecular Devices). Zoxazolamine favors the dopaminergic specification as seen by the increased absolute number of TH$^+$ cells as well as the percentage of TH$^+$ cells among neurons (βIII-tubulin$^+$).

Zoxazolamine enhanced the % of colonies with a neural phenotype. The inventors found that one individual ES cells (ESC) submitted to neural differentiation do not share the same capacity to produce a neural progeny. Thus, a mixture of individual ES cells will induce a mixture of colonies (one colony is derived from one individual ESC), including neural and non-neural colonies. Note that this variability of colonies can be reduced by cloning of ESC, since there is a clonal heterogeneity between individual ES in the culture. However, individual ESC from one clonal ESC line continue to produce a heterogeneous mixture of neural and non-neural cells, suggesting at least stochastic decision for a neural versus non-neural progeny. The effect of zoxazolamine was analyzed for several clones, in its ability to change the % of neural colonies. Zoxazolamine increased the percentage of neural colonies, indicating that the stochastic nature of the decision is in favour of the neural in the presence of zoxazolamine. It results in the enrichment in the number of neurons and thus reduces the heterogeneity of resulting neurons.

Figure 3:
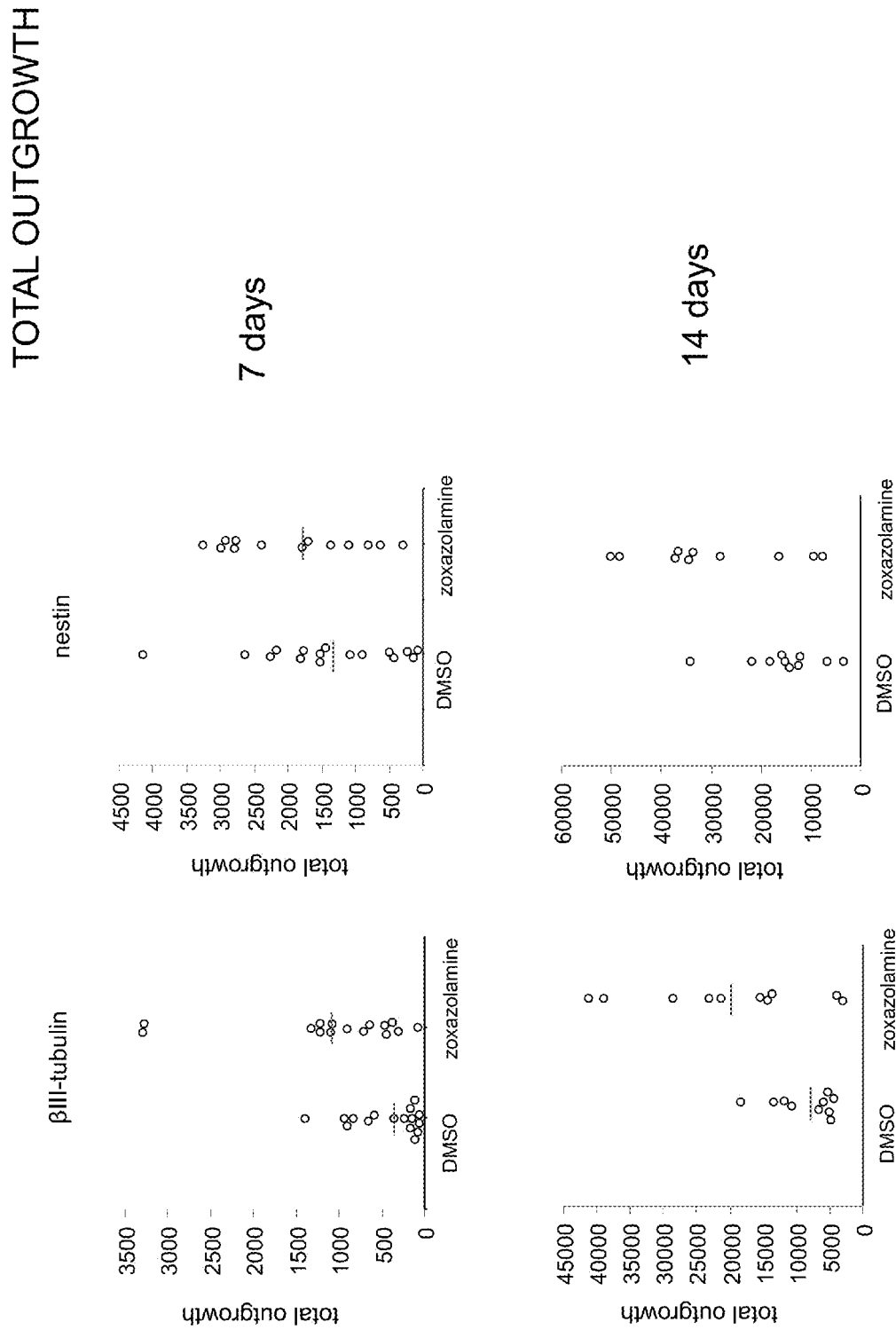
FIG. 3. Zoxazolamine increased total outgrowth of neurites.

As shown in FIG. 3, zoxazolamine also increased neural total outgrowth (represented as total length of all neurites expressing betalll-tubulin or nestin at 7 days and 14 days of differentiation), which results from the number of neurons and their maturation stage: the more the neurons are mature, the more the length of their neurites).

Figure 4:
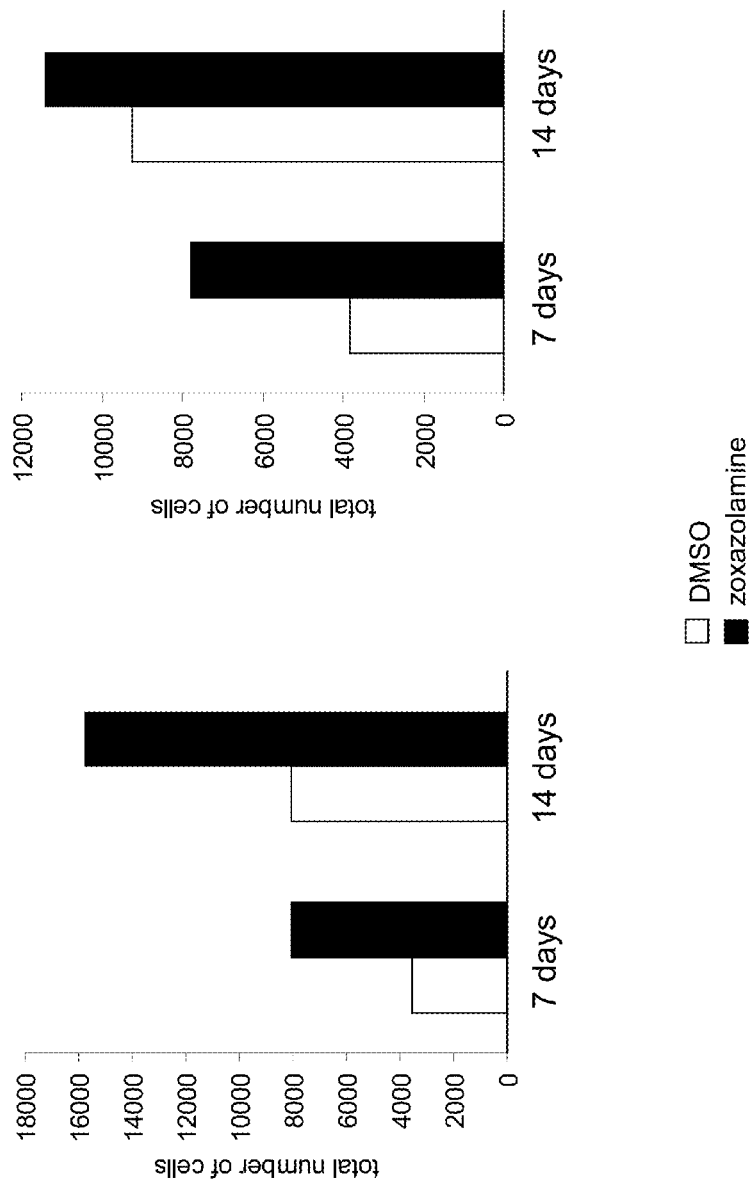
FIG. 4. Zoxazolamine increased number of neurons
Figure 5:
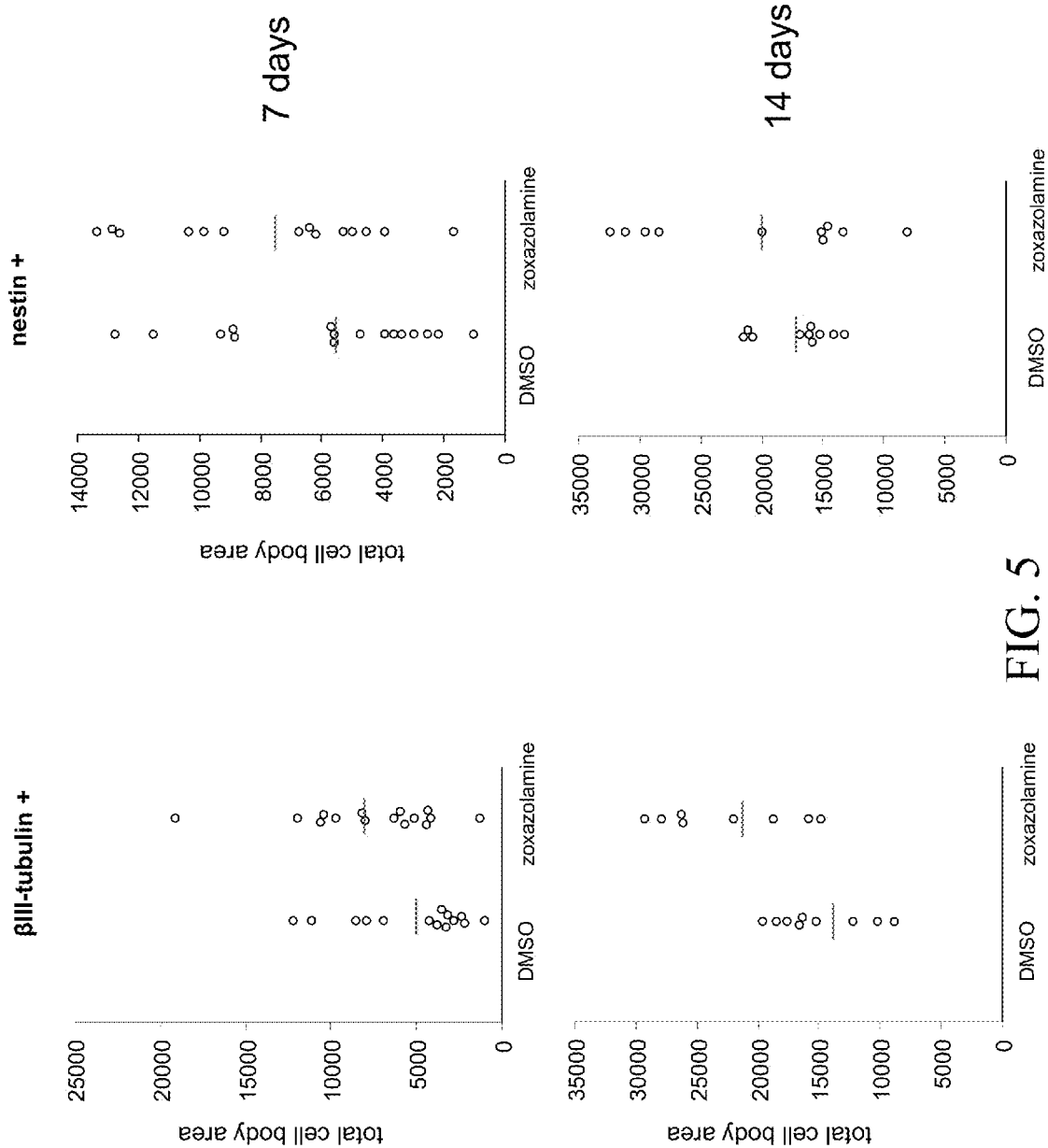
FIG. 5. Zoxazolamine increased neural cell body area.

In addition, Zoxazolamine increased absolute number of neurons at day 7 and day 14 of differentiation (FIG. 4) and absolute number of neural cell bodies at day 16 (FIG. 5) as a neuron includes a cell body and neurites.

Figure 6:
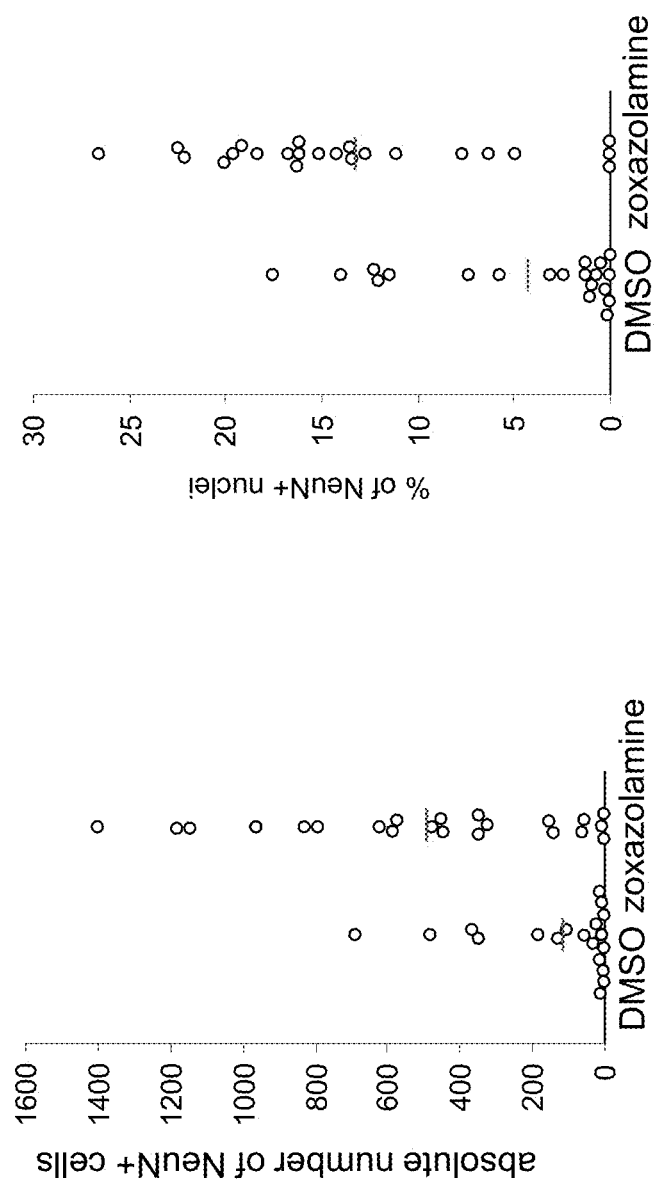
FIG. 6. Zoxazolamine favoured neural maturation.

Zoxazolamine favoured neural maturation as shown in FIG. 6 by an increase in absolute number and percentage of mature neurons (NeuN is a marker of mature stage neurons).

Figure 7:
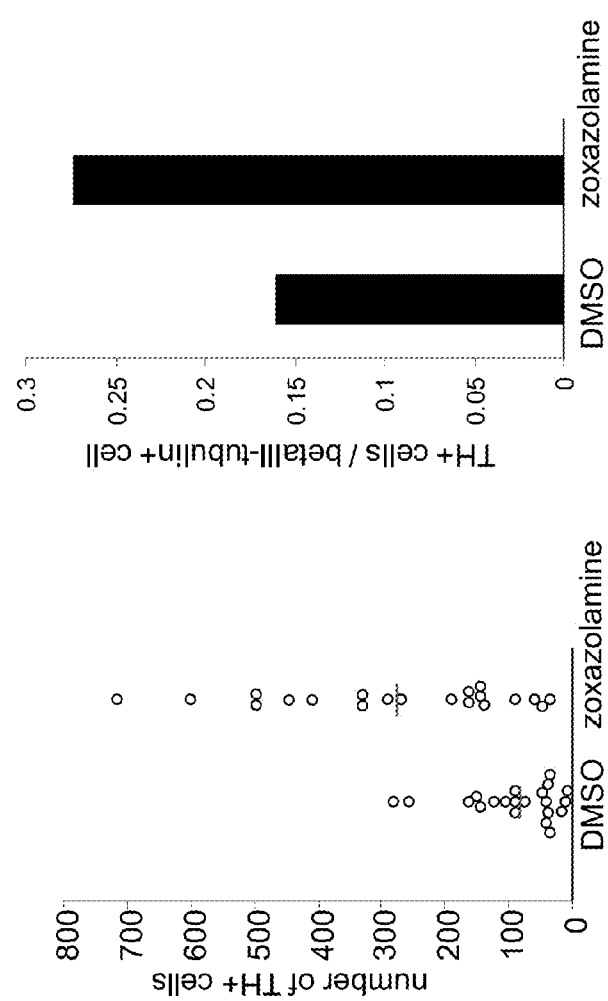
FIG. 7. Zoxazolamine favoured dopaminergic specification of neurons.

Zoxazolamine also favoured dopaminergic specification of neurons as shown by an increase in TH$^+$ cells in FIG. 7 (TH is a marker for dopaminergic neurons).

Figure 8:
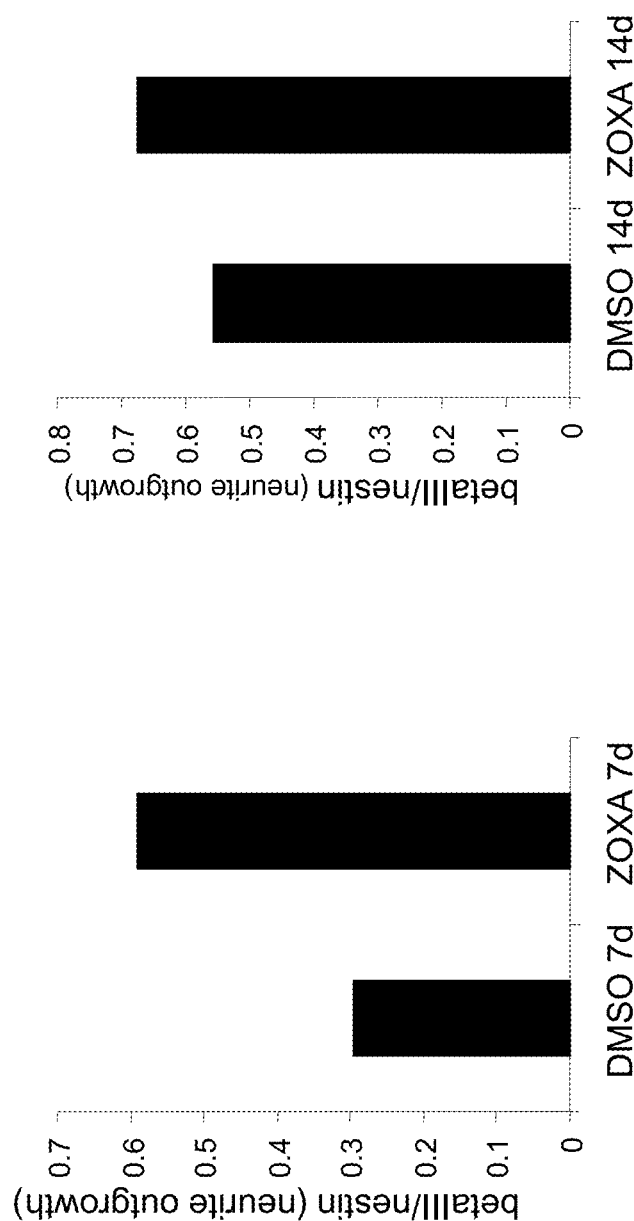
FIG. 8. Zoxazolamine also increased neurite outgrowth.

Zoxazolamine also increase relative neurite outgrowth as the ratio of between the total length of betalll-tublin expressing neurites and the total length of nestin-expressing neurites (FIG. 8).

Figure 9:
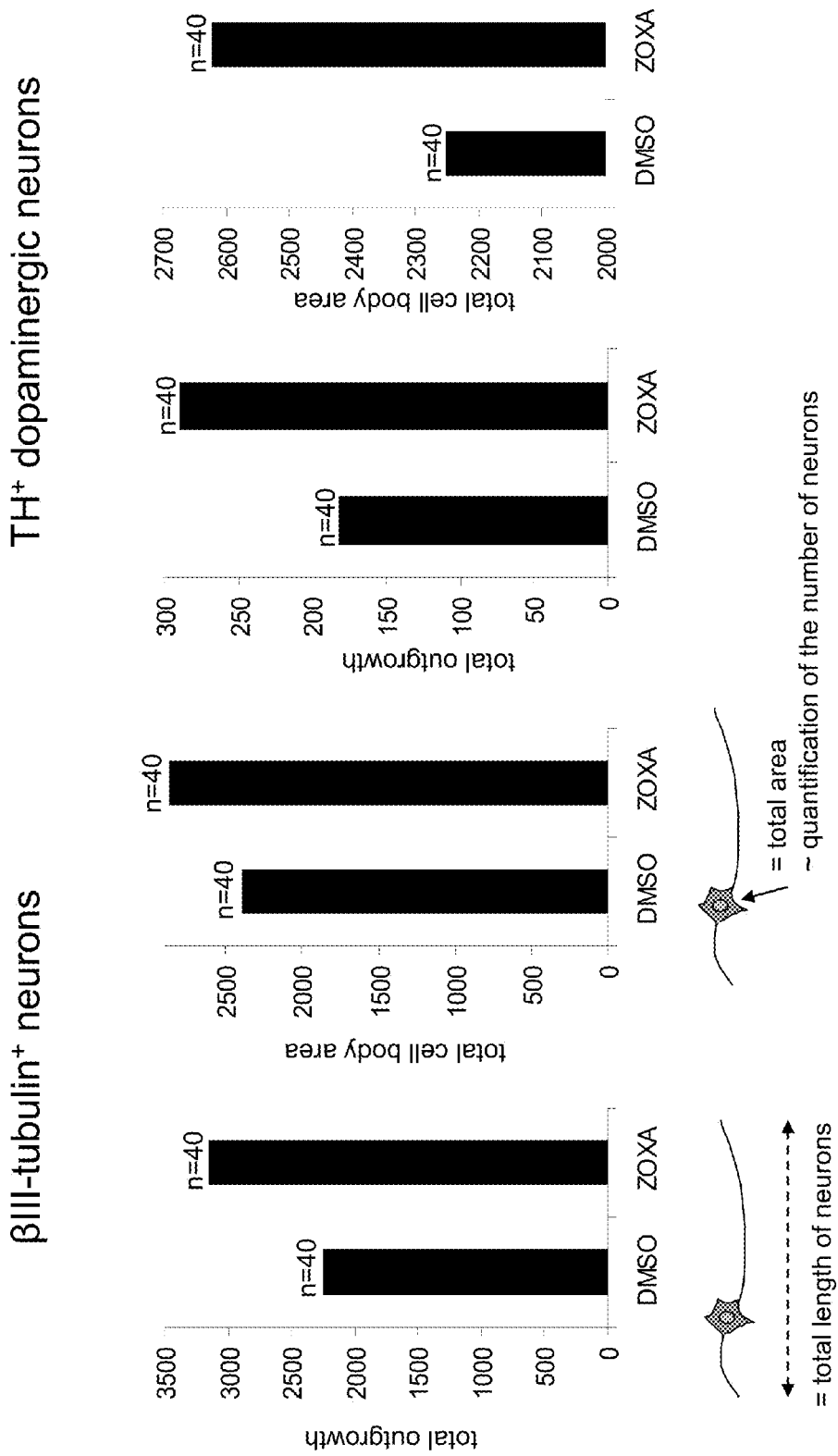
FIG. 9. Effect of zoxazolamine on human ESC neural and dopaminergic differentiation.

The effect of zoxazolamine on neural and dopaminergic differentiation was confirmed in human ES cells as shown in FIG. 9. In these conditions, human ESC were submitted to a conventional neural differentiation protocol which is very different from mouse ESC (mouse and human ESC are not similarly maintained and differentiated towards neurons). Practically, human ES were induced towards floating aggregates in neural induction medium during three weeks. Thereafter, they were dissociated by enzymatic treatment (trypsin) before plating on laminin-coated tissue culture plates for terminal differentiation in neural differentiation medium. Zoxazolamine was at 10 uM in these conditions and exposed to cells for 5 weeks. The amount of neural cells derived from ESC was quantified by picture analysis using the Metamorph software (Molecular devices). Zoxazolamine increased the number of neurons assessed by the increased total area of cell bodies which are immunoreactive against βIII-tubulin and the increased total outgrowth. In accordance, the number of TH$^+$ dopaminergic neurons was increased.

Figure 10A:
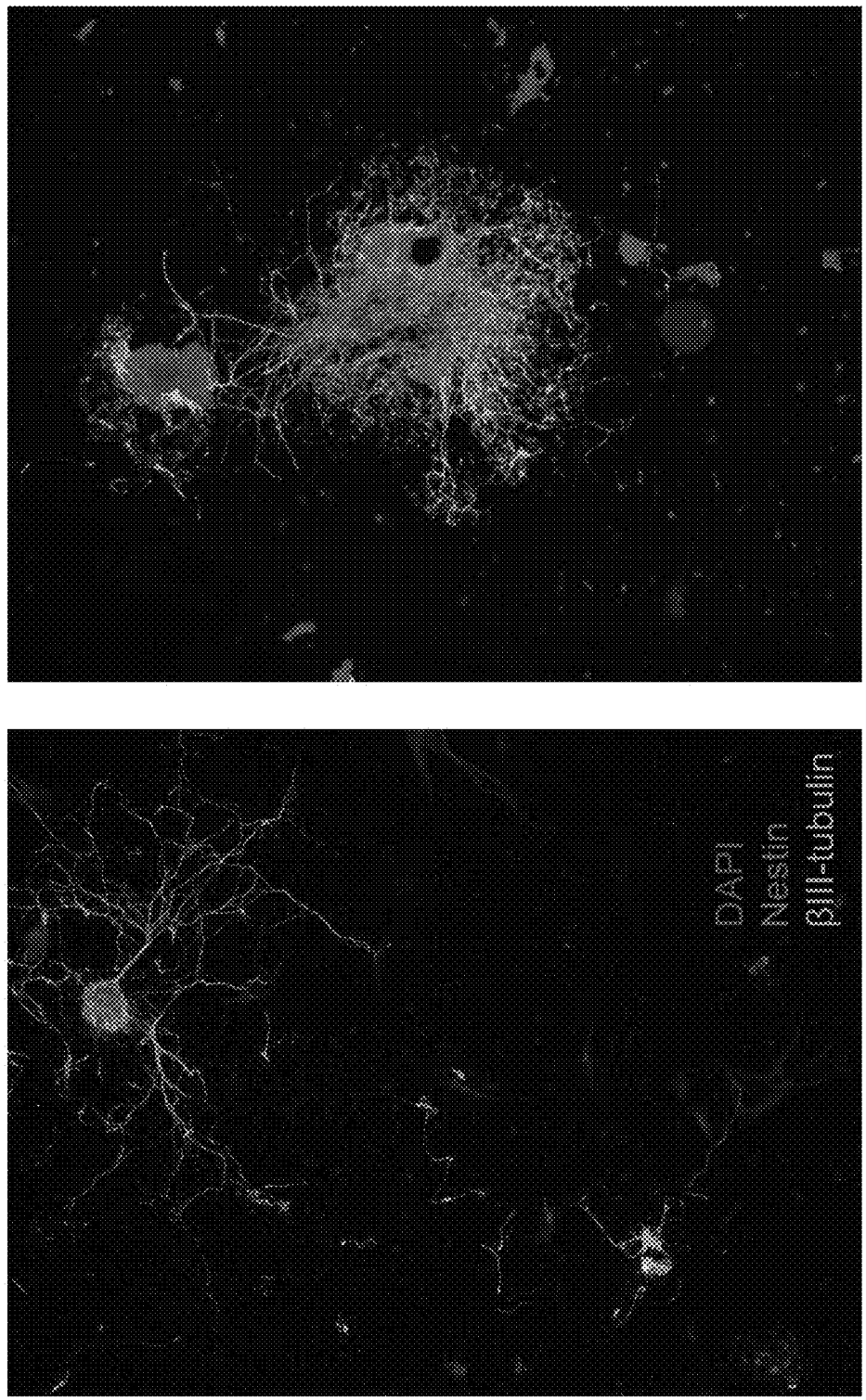
FIGS. 10A-10E. Images of Zoxazolamine-enhanced neural differentiation of mouse ESC.
Figure 10B:
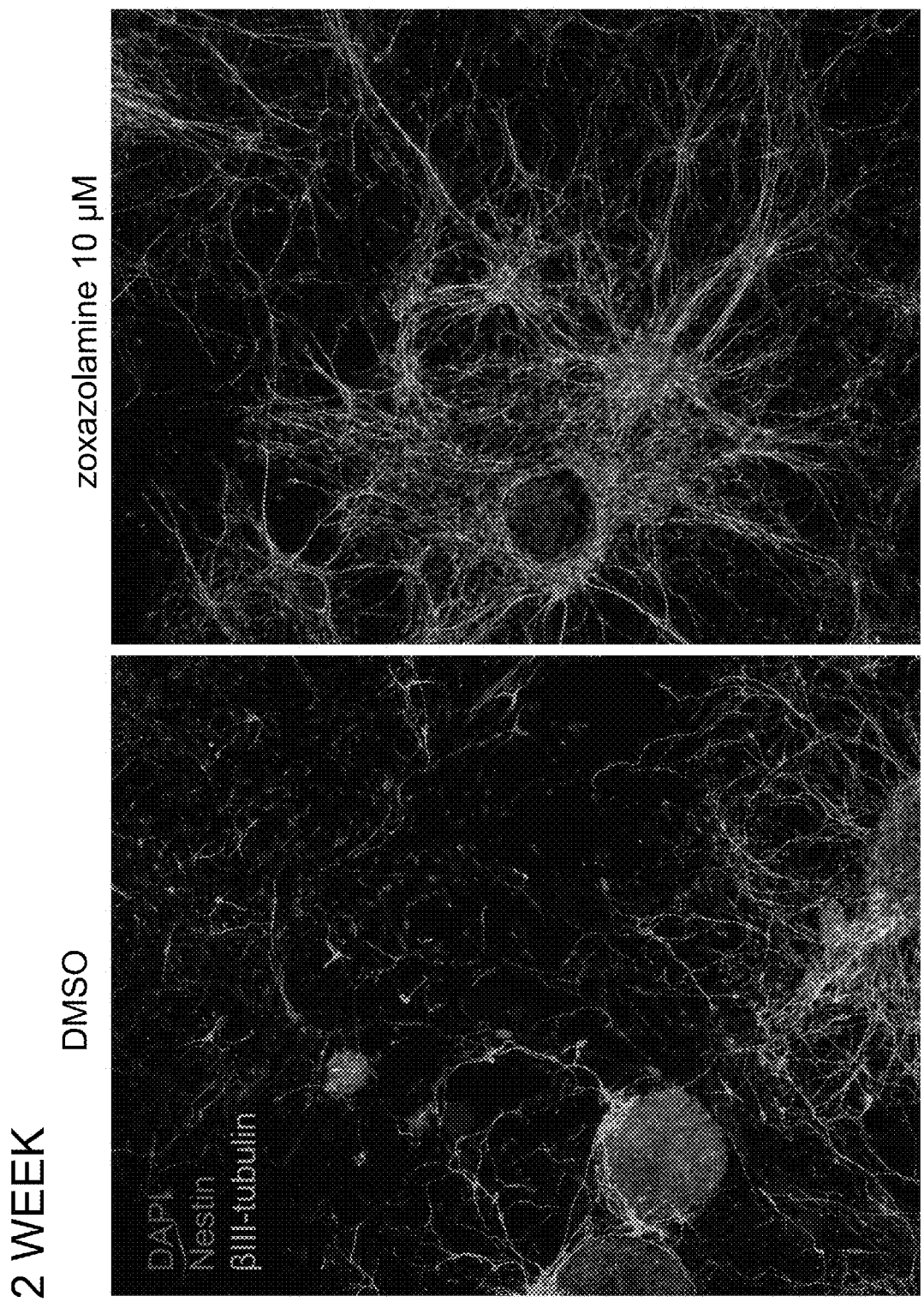
Figure 10C:
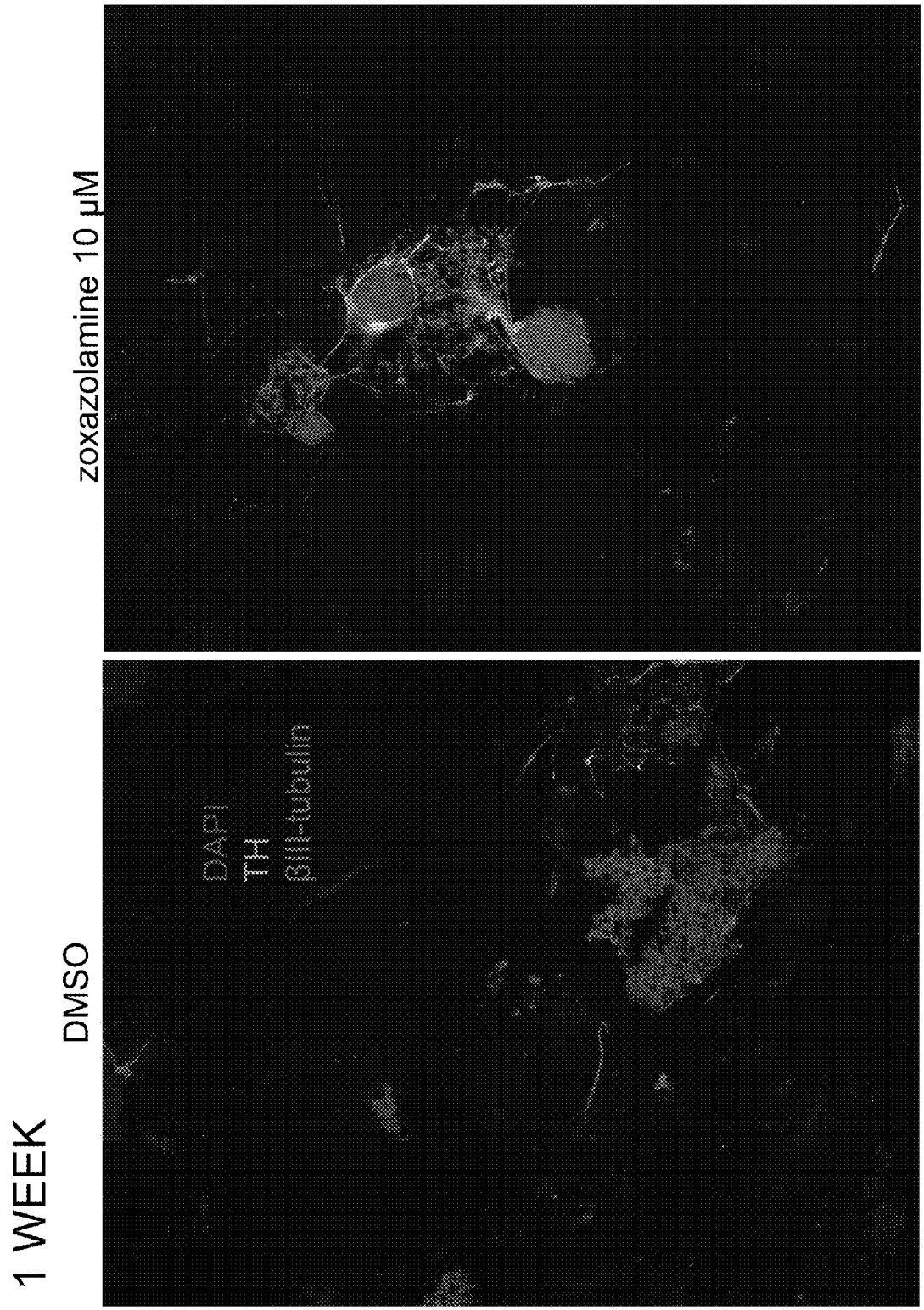
Figure 10D:
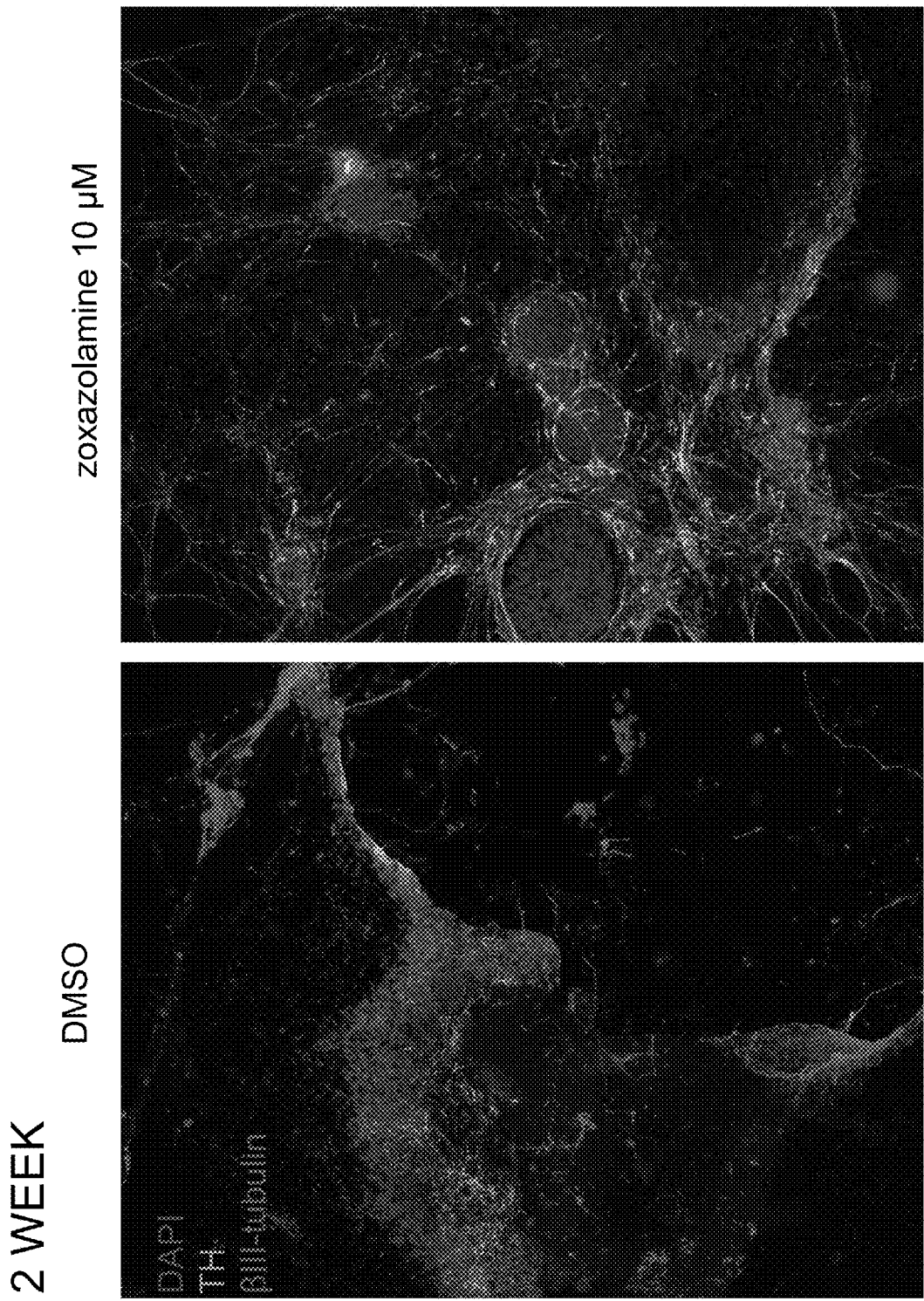
Figure 10E:
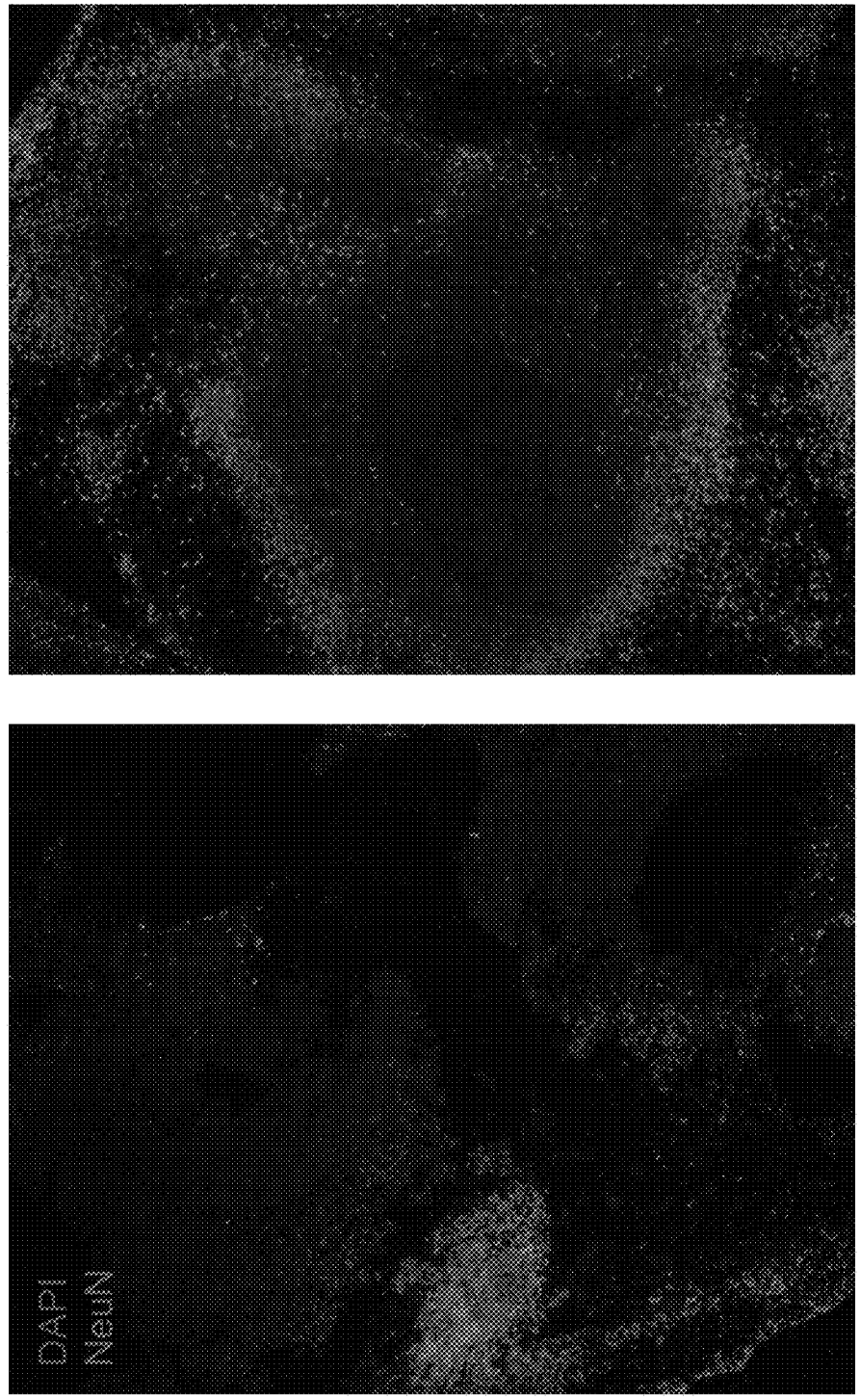

Images of Zoxazolamine-enhanced neural differentiation of mouse ESC after one week (FIG. 10A) or two weeks (FIG. 10B) in the presence of 10 µM zoxazolamine or DMSO were shown with Nestin indicative of neuroepithelial cells and βIII-tubulin indicative of neuronal cells. Zoxazolamine also enhanced dopaminergic differentiation of mouse ESC after one week (FIG. 10C) or two weeks (FIG. 10D) in the presence of 10 µM zoxazolamine or DMSO with TH indicative of neuroepithelial cells and βIII-tubulin indicative of neuronal cells. FIG. 10E shows images of Zoxazolamine-enhanced neuronal maturation of mouse ESC after two weeks in the presence of 10 µM zoxazolamine or DMSO. NeuN is indicative of mature neuronal cells.

Example 5

Dopaminergic Differentiation Effect of Zoxazolamine and its Analogs

Figure 11:
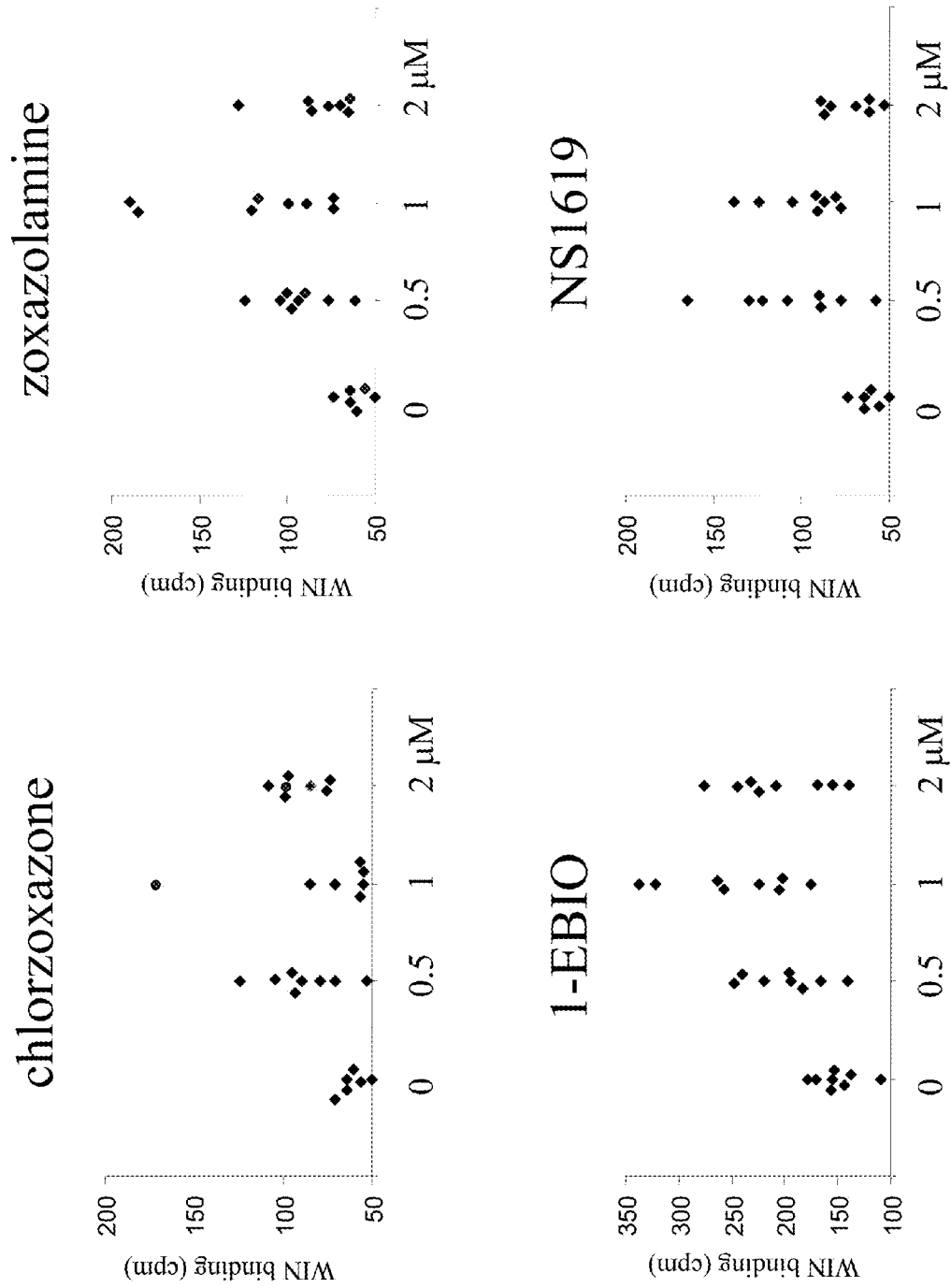
FIG. 11. Effect of zoxazolamine and its analogs on mouse ESC dopaminergic differentiation.

The following structural analogs of zoxazolamine were tested in their ability to modify dopaminergic differentiation of mouse Embryonic Stem Cells (ESC): chlorzoxazone, 1-EBIO, NS1619 (FIG. 11). Zoxazolamine and all of these analogs have the functional capacity to stimulate some potassium channels.

Thus, mouse CGR8 were submitted to neuronal differentiation by co-culture on PA6 feeder cells, in the presence or not in the medium of zoxazolamine or its analogs. Mouse ESC maintenance and differentiation methods and materials were the same as described in Example 2. The optimal ratio ESC CGR8/PA6 feeder cell in these conditions was 1000/125 000 PA6 in 2 ml differentiation medium containing zoxazolamine. Note that PA6 were initially seeded on a glass coverslip. Several concentrations of analogs diluted in DMSO were tested. DMSO was used as the vehicle alone control.

A conventional binding assay described in EXAMPLE 3 was used to quantify, after 16 days unless otherwise specified, the amount of dopaminergic neurons. After 16 days, dopaminergic neurons were quantified by their ability to incorporate the radioactive ligand WIN. After 16 days of differentiations, cells were incubated with 5 nM of [$^3$H] Win35, 428 for 1 hour and then washed by binding buffer for 1 minute, following by direct counting using liquid scintillation counter (WALLAC) for dopaminergic neuron quantification.

Thus, the measurement of the cell radioactivity expressed in count per minute (cpm) reflect the amount of dopaminergic neurons for each condition. The experiment was performed several times and one representative experiment is presented. In one experiment, each compound at a defined concentration was tested in octoplicates. At concentrations ranging around 1 μM, all the analogs induced a moderate but significant increase of the number of dopaminergic neurons. Thus, potassium channel activators analogs to zoxazolamine enhanced in vitro dopaminergic differentiation of mouse ESC.

Example 6

Neurotoxicology Testing Platform

Figure 12:
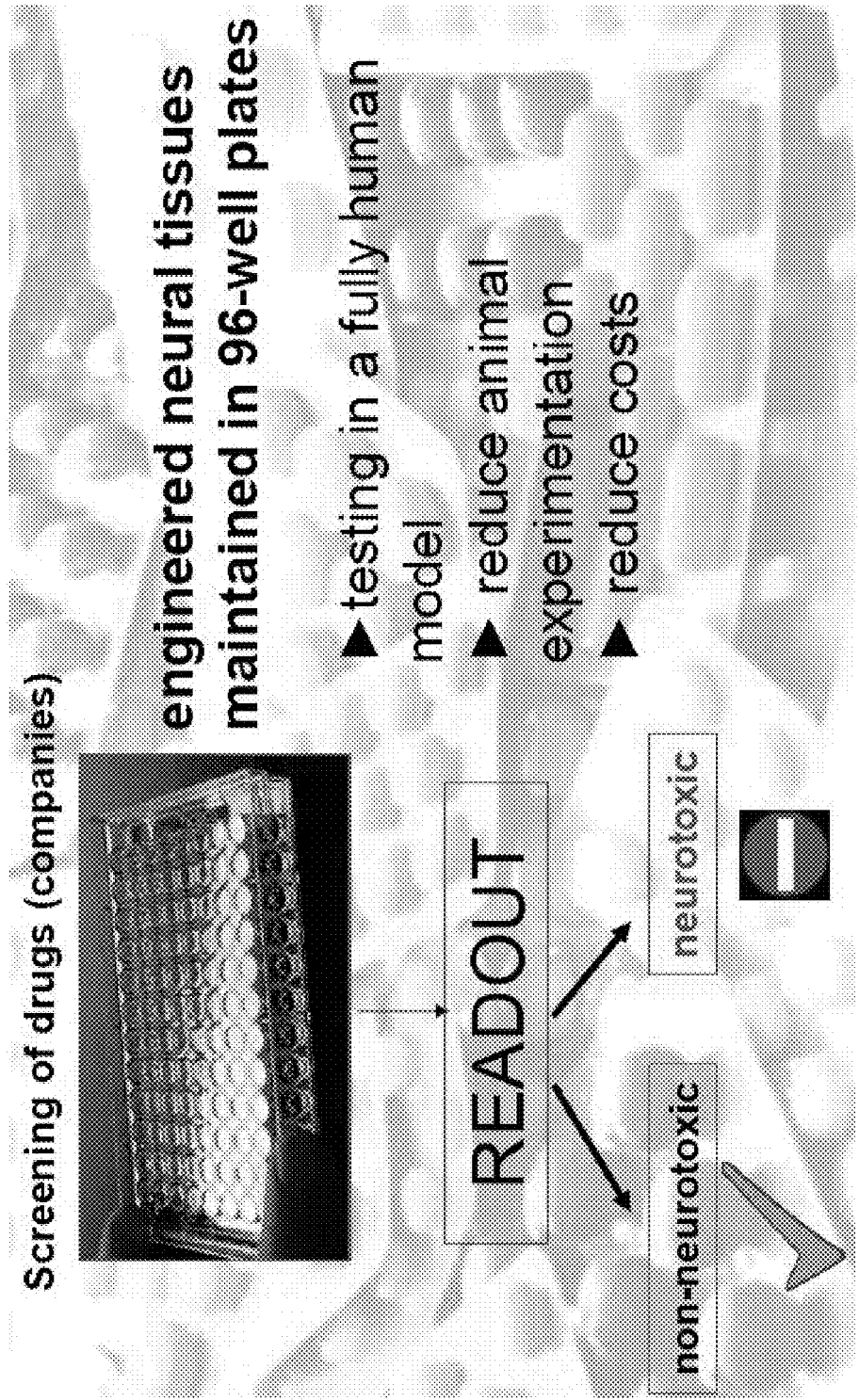
FIG. 12. Establishment of a neurotoxicology testing platform.
Figure 13:
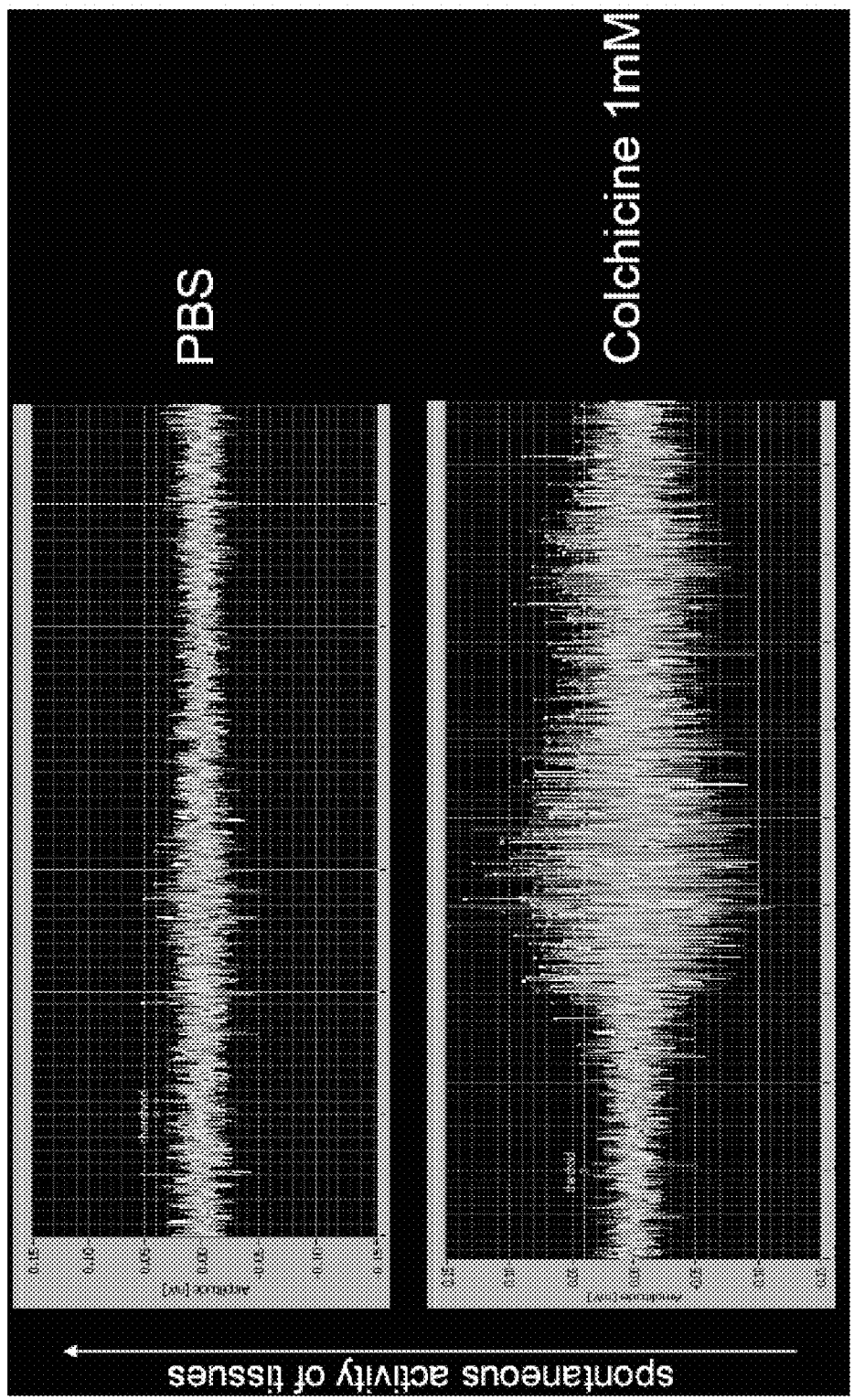
FIG. 13. Validation of the neurotoxicology testing platform.
Figure 14:
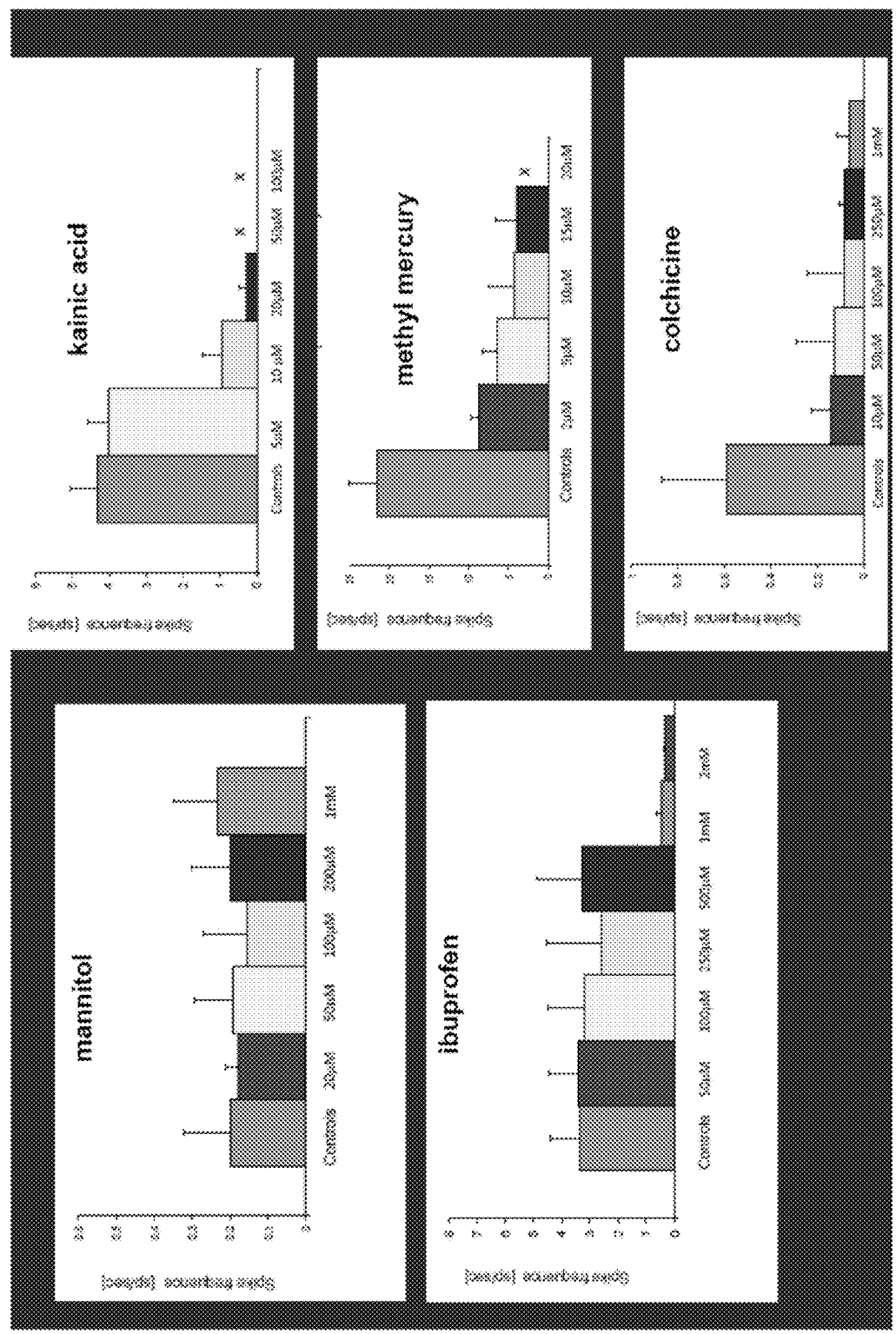
FIG. 14. Putative neurotoxics were tested for neurotoxicity in mouse ENTs.
Figure 15:
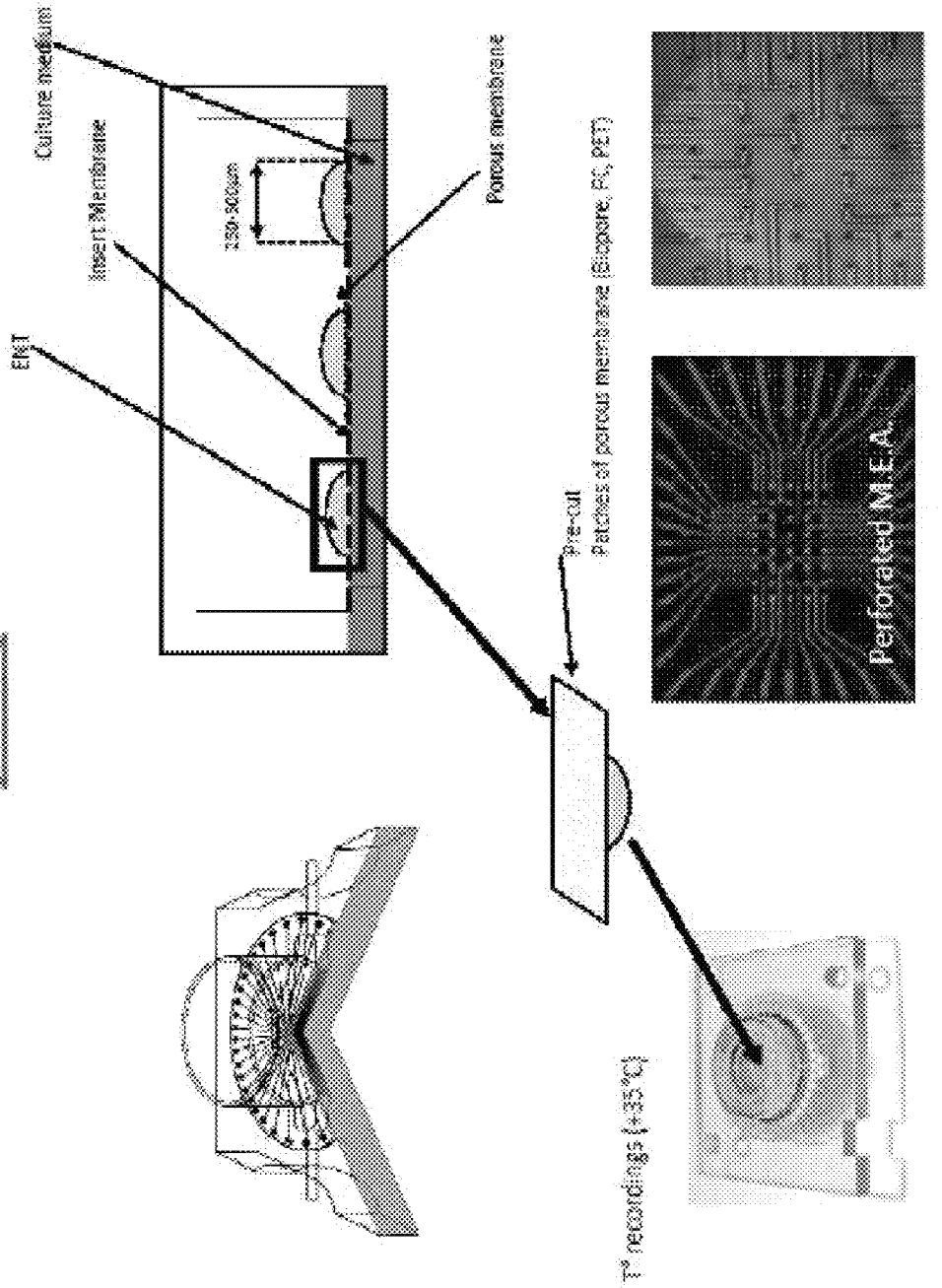
FIG. 15. Electrophysiological approach of testing ENT activity.

Engineered neural tissues (ENTs) (a similar scheme could be applied to dopaminergic neurons provided according to certain aspects of the present invention) can be used for establishment of a neurotoxicology testing platform (FIG. 12). The epileptogenic activity of colchicine was demonstrated in ENTs generated herein (FIG. 13). Mouse ENTs differentiated for 21 days were exposed to putative neurotoxic for 24 hours and spontaneous electrical activity was measured for the neurotoxicity testing (FIG. 14). The electric activity of ENTs could be tested on a multi-electrode array (M.E.A.) as shown in FIG. 15. Electrophysiological characterizations of ENTs include characterization of spontaneous activity such as spike frequency, spike amplitude, burst frequency (number of bursts per second), or number of spikes per burst, or characterization of evoked filed potentials such as amplitude of responses, paired-pulse inhibition, or input/output curve. The electrophysiological characterization of ENTs can be carried out by a multi-electrode array (FIG. 16).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 5,843,780
U.S. Pat. No. 6,200,806
U.S. Pat. No. 6,833,269
U.S. Pat. No. 6,833,269
U.S. Pat. No. 7,029,913
U.S. Patent Application 2008/0233610
European Patent Application EP1970446A1
*A practical approach* (Robertson, Ed.), IRL Press Ltd. 1987.
Allegrucci and Young, *Hum. Reprod. Update*, 13:103-120, 2007.
Amit et al., *Dev. Bio.*, 227:271-278, 2000.
*Animal Cell Culture* (Freshney, Ed., 1987)
Anthony et al., *Neuron.*, 41:881-890, 2004.
Barberi et al., *Nat. Biotechnol.*, 21(10):1200-1207, 2003.
Bauer and Patterson, *J. Neurosci.*, 26(46):12089-12099, 2006.
Bayatti et al., *Cereb. Cortex*, 18(7):1536-1548, 2007.
Byrne et al., *Nature*, 450(7169):497-502, 2007.
Campbell et al., *Proc. Natl. Acad. Sci. USA*, 99(12):7877-7882, 2002.
Chalfie et al., *Science*, 263(5148):802-805, 1994.
Chen et al., *J. Am. Chem. Soc.*, 126(2):410-411, 2004.
Chen et al., *Mol. Biosyst.*, 2(1):18-24, 2006b.
Chen et al., *Proc. Natl. Acad. Sci. USA*, 103(46):17266-17271, 2006a.
Chen et al., *Proc. Natl. Acad. Sci. USA*, 104(25):10482-10487, 2007.
Cho et al., *Proc. Natl. Acad. Sci. USA*, 105:3392-3397, 2008.
*Current Protocols in Molecular Biology and Short Protocols in Molecular Biology*, 3rd Edition (Ausubel et al., Eds.), 1987 & 1995.
Desbordes et al., *Cell Stem Cell*, 2(6):602-612, 2008.
Ding et al., *Proc. Natl. Acad. Sci. USA*, 100(13):7632-76337, 2003.
Doetsch et al., *Cell*, 97:703-716, 1999.
Eiraku et al. *Cell Stem Cell.* 3(5):519-32, 2008.
Elkabetz et al., *Genes Dev.*, 22:152-165, 2008.
Fallon et al., *Proc. Natl. Acad. Sci. USA*, 97(26):14686-14691, 2000.
Feng et al., *Neuron.*, 12:895-908, 1994.
Foti et al., *J. Cell Biol.*, 139:37-47, 1997.
Gaines, *Urol Nurs.*, 24(3):207-209, 2004.
Garcia et al., *Nat. Neurosci.*, 7:1233-1241, 2004.
*Gene Transfer Vectors for Mammalian Cells* (Miller & Calos, Eds.), 1987.
Gotz et al., *Brain Res Bull.*, 57:777-788, 2002.

Gould, *Nat. Rev. Neurosci.*, 8:481-488, 2007.
*Guide to Techniques in Mouse Development* (Wasserman et al. Eds.), Academic Press 1993.
Gustafsson et al., *Dev. Cell.*, 9:617-628, 2005.
*Handbook of Pharmaceutical Salts: Properties, Selection and Use* (Stahl & Wermuth, Eds., Verlag Helvetica Chimica Acta, 2002.
Haubensak et al., *Proc. Natl. Acad. Sci. USA*, 101:3196-3201, 2004.
Innis et al., *Proc. Natl. Acad. Sci. USA*, 85(24):9436-9440, 1988.
Itoh et al., *Exp. Hematol.*, 17(2):145-153, 1989.
Itoh et al., *Exp. Hematol.*, 17:145-153, 1989.
Itskovitz-Eldor et al., *Mol. Med.*, 6:88B95, 2000.
Joannides et al., *Stem Cells*, 25:731-737, 2007.
Joannides et al., *Brain*, 130:1263-1275, 2007.
Johansson et al., *Cell*, 96:25-340, 1999.
Kim et al., *Neurochem. Res.*, 32(8):1399-1406, 2007.
Lee et al., *Nat. Biotechnol.*, 25:1468-1475, 2007.
Lee et al., *Stem Cells*, 25:1931-1939, 2007.
Malatesta et al., *Neuron.*, 37:751-764, 2003.
Mallat et al., *Curr. Opin. Neurobiol.*, 15:101-107, 2005.
Martin, *Proc. Natl. Acad. Sci. USA*, 78:7634B7638; 1982.
Merkle and Alvarez-Buylla, *Curr. Opin. Cell Biol.*, 18:704-709, 2006.
Metallo et al., *Stem Cells*, 26(2): 372-380
Mo and Zecevic, *Cereb Cortex*, 18(6):1455-1465, 2007.
Nat et al., *Glia.*, 55(4):385-399, 2007.
O'Connor et al., *Stem Cells*, 26(5):1109-1116, 2008.
Osafune et al., *Nat. Biotechnol.*, 26:313-315, 2008.
Perrier et al., *Proc. Natl. Acad. Sci. USA*, 101:12543-12548, 2004.
Perrier et al, *Proc. Natl. Acad. Sci. USA*, 101(34):12543-12125, 2004.
Pruszak et al., *Stem Cells*, 25(9):2257-2268, 2007.
Quinones-Hinojosa et al., *J. Comp. Neurol.*, 494:415-434, 2006.
Rathjen et al., *Reprod. Fertil. Dev.*, 10:31, 1998.
Remington's Pharmaceutical Sciences" 15th Edition, pages 1035-1038 and 1570-1580
Reubinoff et al, *Nature Biotech.*, 18:399, 2000.
Reubinoff et al., *Nat. Biotechnol.*, 18:399B404, 2000.
Rezaie et al., *Microsc. Res. Tech.*, 45:359-382, 1999.
Rietze and Reynolds, *Methods Enzymol.*, 419:3-23, 2006.
Roach et al., *Eur. Urol.*, 23:82B87, 1993.
Roussa and Krieglstein, *Cell Tissue Res.*, 318:23-33, 2004.
Sachinidis et al., *Cell Physiol. Biochem.*, 18(6):303-314, 2006.
Sarichelou et al., *Cell Death Differ.*, 15(4):700-707, 2008.
Schulz et al., *Stem Cells*, 22:1218-1238, 2004.
Smith, In: *Origins and Properties of Mouse Embryonic Stem Cells*, Annu Rev. Cell. Dev. Biol., 2000.
Sonntag et al., *Stem Cells*, 25:411-418, 2007.
Stern, *Development*, 132:2007-2021, 2005.
Stoppini et al., *J. Neurosci. Methods*, 37(2):173-182, 1991.
Storch et al., *Exp. Neurol.*, 170:317-325, 2001.
Studer et al., *J. Neurosci.*, 20:7377-7383, 2000.
Suter et al., *J Stem Cells*. January, 63-72, 2007.
Suter et al., *Stem Cells*, 24(3):615-623, 2006.
Svendsen et al., *Brain Pathol.*, 9(3):499-513, 1999.
Takahashi and Yamanaka, *Cell*, 126:663-676, 2006.
Takahashi et al., *Cell*, 126(4):663-676, 2006.
Takahashi et al., *Cell*, 126(4):663-76, 2007.
Takahashi et al., *Cell*, 131:861-872, 2007.
Thiebaud et al., *IEEE Trans. Biomed. Eng.*, 44:1159-1163, 1997.
Thomson and Marshall, *Curr. Top. Dev. Biol.*, 38:133-165, 1998.
Thomson and Odorico, *J. Trends. Biotechnol.*, 18:53B57, 2000.
Thomson et al. *Proc. Natl. Acad. Scie. USA*, 92:7844-7848, 1995.
Thomson et al., *Science*, 282:1145, 1998.
van Vliet et al., *Neurotoxicology*, 28:1136-1146, 2007.
Vazin et al., *Stem Cells*, 26:1517-1525, 2008.
Wiles, *Meth. Enzymol.*, 225:900, 1993.
Wilson and Edlund, *Nat. Neurosci.*, 4(Suppl):1161-1168, 2001.
Wu et al., *Proc. Natl. Acad. Sci. USA*, 104:13821-13826, 2007.
Xu et al., *Nat. Biotechnol.*, 19:971-974, 2001.
Yan et al., *Stem Cells*, 23:781-790, 2005.
Yang et al., *Stem Cells*, 26:55-63, 2008.
Ying et al., *Cell*, 115:281-292, 2003.
Yu and Thompson, *Genes Dev.* 22(15):1987-97, 2008.
Yu et al., *Science*, 318:1917-1920, 2007.

The invention claimed is:

1. A method of enhancing differentiation of stem cells into dopaminergic neural cells comprising inducing neural cell differentiation of stem cells in the presence of zoxazolamine (Zol) or a structural analog of Zol having the capacity to stimulate potassium channels for a sufficient amount of time to differentiate the stem cells into dopaminergic neural cells, wherein said stem cells are pluripotent stem cells or neural stem cells and wherein the presence of Zol or said analog increases the number of dopaminergic neurons compared to inducing neural cell differentiation of pluripotent cells or neural stem cells in the absence of Zol or said analog.

2. The method of claim 1, wherein the zoxazolamine or structural analog has a formula of:

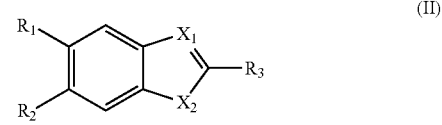

(II)

wherein $R_1$ is chloro, $X_1$ is N and $X_2$ is O.

3. The method of claim 1, wherein the zoxazolamine or structural analog is zoxazolamine.

4. The method of claim 1, wherein the zoxazolamine or structural analog is 5-chloro-2-hydroxybenzoxazole (chlorzoxazone).

5. The method of claim 1, wherein the pluripotent cells are embryonic stem cells or induced pluripotent stem cells.

6. The method of claim 1, further comprising evaluating the dopaminergic neurons for one or more characteristics of dopaminergic neuronal cells.

7. The method of claim 1, further comprising contacting the dopaminergic neurons with a test compound and determining if the test compound has a pharmacological or toxicological impact on said dopaminergic neuron.

* * * * *